(12) United States Patent
Park et al.

(10) Patent No.: US 7,955,512 B2
(45) Date of Patent: Jun. 7, 2011

(54) MEDICAL DEVICES HAVING TEXTURED SURFACES

(75) Inventors: Eunsung Park, Plymouth, MN (US);
Catherine E. Taylor, Fridley, MN (US);
Kevin Casey, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 1150 days.

(21) Appl. No.: 11/674,607

(22) Filed: Feb. 13, 2007

(65) Prior Publication Data
US 2007/0225785 A1 Sep. 27, 2007

Related U.S. Application Data

(60) Provisional application No. 60/813,598, filed on Feb. 13, 2006, provisional application No. 60/805,451, filed on Jun. 21, 2006, provisional application No. 60/822,866, filed on Aug. 18, 2006.

(51) Int. Cl.
*B44C 1/22* (2006.01)
(52) U.S. Cl. ........... 216/58; 216/56; 216/63; 216/64; 216/67; 216/68; 216/75
(58) Field of Classification Search .......... None
See application file for complete search history.

(56) References Cited

U.S. PATENT DOCUMENTS

| | | | |
|---|---|---|---|
| 5,011,494 A | 4/1991 | von Recum et al. | |
| 5,188,800 A * | 2/1993 | Green et al. | 134/1 |
| 5,219,361 A | 6/1993 | von Recum et al. | |
| 5,223,691 A | 6/1993 | Frei et al. | |
| 5,260,093 A * | 11/1993 | Kamel et al. | 427/2.25 |
| 5,326,584 A * | 7/1994 | Kamel et al. | 427/491 |
| 5,336,263 A | 8/1994 | Ersek et al. | |
| 5,348,788 A | 9/1994 | White | |
| 5,405,385 A | 4/1995 | Heimke et al. | |
| 5,507,804 A * | 4/1996 | Llanos | 623/6.11 |
| 5,549,670 A | 8/1996 | Young et al. | |
| 5,578,079 A * | 11/1996 | Kamel et al. | 623/6.57 |
| 5,697,997 A * | 12/1997 | Aronsson et al. | 65/32.1 |
| 5,753,567 A * | 5/1998 | Banan et al. | 438/720 |
| 5,980,973 A | 11/1999 | Onyekaba et al. | |
| 6,008,430 A | 12/1999 | White | |
| 6,033,582 A * | 3/2000 | Lee et al. | 216/37 |
| 6,078,840 A | 6/2000 | Stokes | |
| 6,129,759 A | 10/2000 | Chambers | |
| 6,258,123 B1 | 7/2001 | Young et al. | |
| 6,263,249 B1 | 7/2001 | Stewart et al. | |
| 6,419,491 B1 * | 7/2002 | Ricci et al. | 433/173 |
| 6,464,889 B1 | 10/2002 | Lee et al. | |
| 6,481,370 B2 | 11/2002 | Kazumi et al. | |
| 6,599,322 B1 | 7/2003 | Amrich et al. | |
| 7,018,418 B2 | 3/2006 | Amrich et al. | |
| 7,055,237 B2 | 6/2006 | Thomas | |
| 7,147,647 B2 | 12/2006 | Onyekaba et al. | |

(Continued)

FOREIGN PATENT DOCUMENTS

EP 0850604 A2 7/1998

(Continued)

OTHER PUBLICATIONS

Kang M et al. "Nanowell-array surfaces prepared by argon plasma etching through a nanopore alumina mask." Langmuir 21:8429-8438, 2005, published on web May 25, 2005.

(Continued)

*Primary Examiner* — Anita K Alanko

(57) ABSTRACT

Disclosed are medical devices having textured surfaces and related methods for texturing. Methods of surface texturing using gas-phase plasma provide medical devices with myriad complex surface morphologies.

31 Claims, 28 Drawing Sheets

U.S. PATENT DOCUMENTS

| | | | |
|---|---|---|---|
| 7,431,959 B1 * | 10/2008 | Dehnad | 427/2.21 |
| 2001/0041874 A1 | 11/2001 | Reydel | |
| 2002/0009604 A1 * | 1/2002 | Zamora et al. | 428/450 |
| 2004/0148015 A1 | 7/2004 | Lye et al. | |
| 2005/0070989 A1 | 3/2005 | Lye et al. | |
| 2005/0084515 A1 | 4/2005 | Udipi et al. | |
| 2006/0100716 A1 * | 5/2006 | Lerf | 623/23.5 |

FOREIGN PATENT DOCUMENTS

| | | |
|---|---|---|
| WO | 9320474 | 10/1993 |
| WO | 99/36276 A1 | 7/1999 |
| WO | 0158374 | 8/2001 |
| WO | 2005000094 | 1/2005 |
| WO | WO 2007095549 A3 * | 5/2008 |

OTHER PUBLICATIONS

Benck, E.C. et al, "Investigations in the sheath region of a radio frequency biased inductively coupled discharge." Journal of Vacuum Science and Technology 16(1):306-315, Jan./Feb. 1998.

* cited by examiner

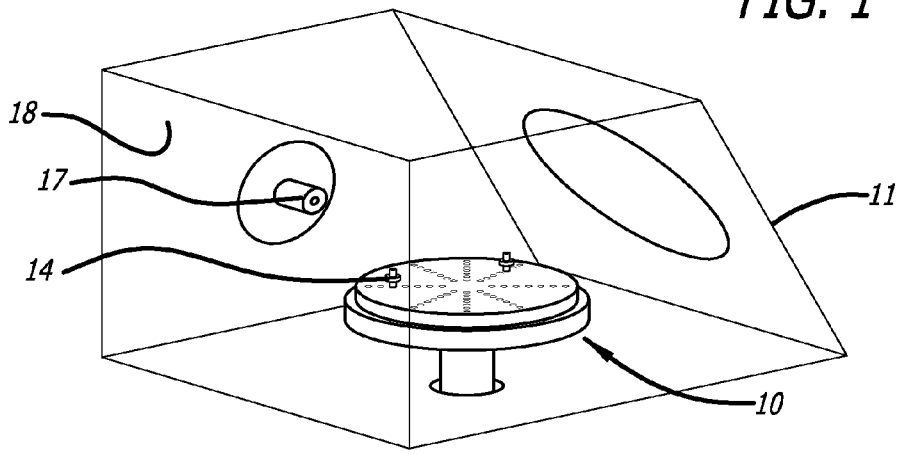
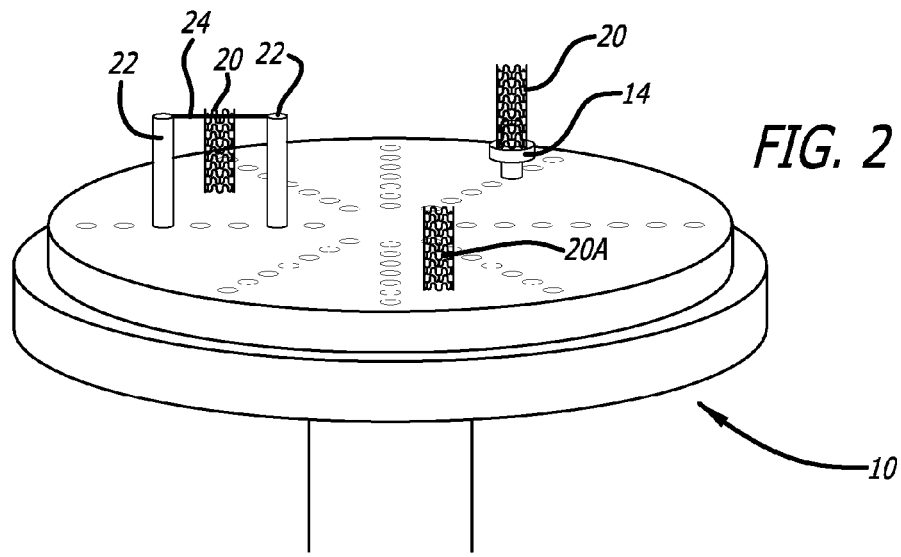
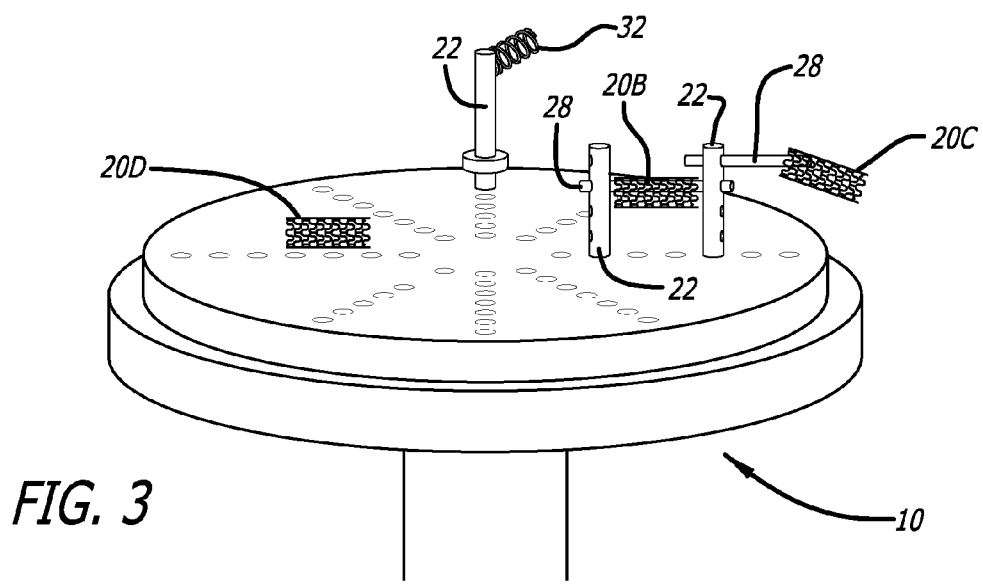

| | at % C | at % O | at % Si | at % Mo | at % Co | at % Ni | at % Cr |
|---|---|---|---|---|---|---|---|
| Ring 1 | 42.4 | 28.7 | 2.3 | 7.7 | 9.8 | 5.7 | 3.5 |
| Ring 7 | 46.6 | 30.1 | nd | 3.7 | 12.4 | 4.3 | 3.2 |
| Ring 15 | 41.2 | 31 | nd | 1.5 | 15.2 | 7.3 | 3.5 |
| MP35N (stent) Reference | 51.5 | 26.5 | 3.0 | 4.0 | 2.9 | 6.9 | 4.3 |

FIG. 24A
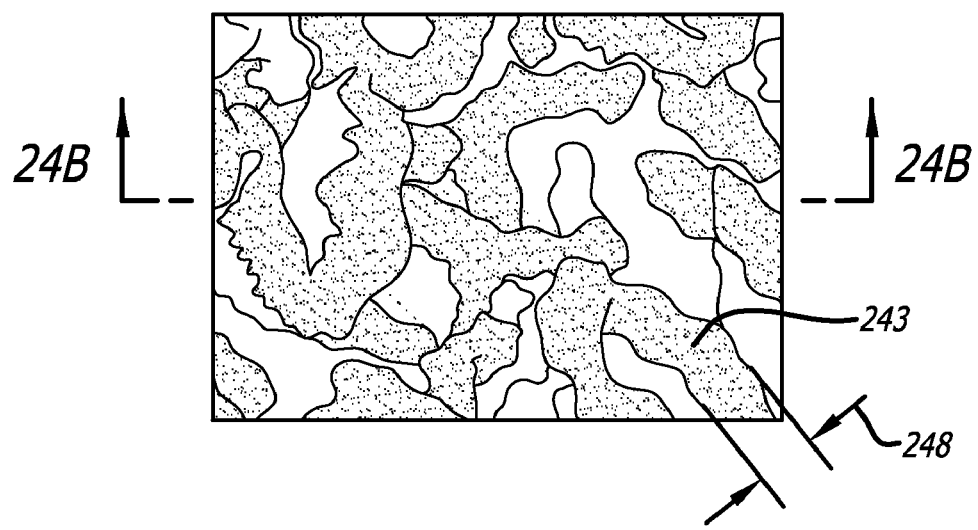
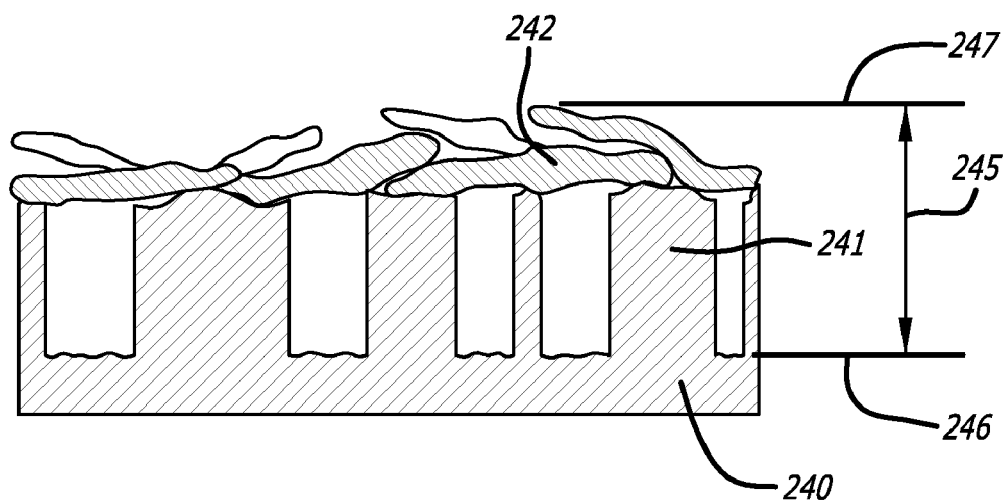
FIG. 24B

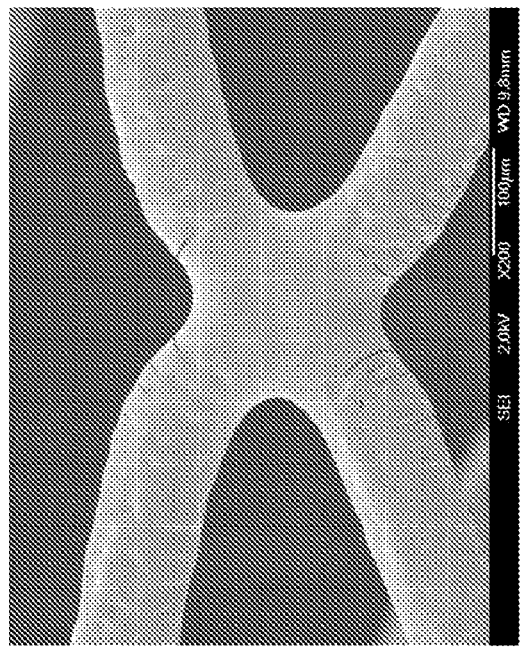
FIG. 30

MEDICAL DEVICES HAVING TEXTURED SURFACES

CROSS REFERENCE TO RELATED APPLICATIONS

The present application claims the benefit under 37 CFR §119(e) of U.S. Provisional Application Nos. 60/813,598 filed Feb. 13, 2006, 60/805,451 filed Jun. 21, 2006 and 60/822,866 filed Aug. 18, 2006, the contents of which are incorporated by reference herein in their entirety.

FIELD OF THE INVENTION

The present invention provides medical devices having textured surfaces and related methods. Specially, the present invention provides implantable medical devices having surfaces textured to form specific morphologies. In one example, the textured surface is provided using radio-frequency-generated (RF-generated) plasma. In another example, the implantable medical device is a vascular stent.

BACKGROUND OF THE INVENTION

The implantation of medical devices has become a relatively common technique for treating a variety of medical or disease conditions within a patient's body. Depending upon the conditions being treated, today's medical implants can be positioned within specific portions of a patient's body where they can provide beneficial functions for periods of time ranging from days to years. A wide variety of medical devices can be considered implants for purposes of the present invention. Such medical devices can include structural implants such as stents and internal scaffolding for vascular use, replacement parts such as vascular grafts, or in-dwelling devices such as probes, catheters and microparticles for monitoring, measuring and modifying biological activities within a patient's cardiovascular system. Other types of medical implants for treating different types of medical or disease conditions can include in-dwelling access devices or ports, valves, plates, barriers, supports, shunts, discs, and joints, to name a few.

However medical device may migrate from the initial implantation site resulting in loss of efficacy or serious injury. Polished bare metal vascular stents may migrate before endothelialization can occur and exacerbate the initial restriction in coronary blood flow. Moreover, directly coating polished bare metal stents with drugs can result in an immediate release of the drug rather than controlled release. As a result the drug's beneficial effects are diminished, or in some cases localized drug toxicity may occur.

An innovative solution to combat the aforementioned problems with polished bare metal medical devices, particularly vascular stents, has been the development of coating technologies. Polymeric coatings, both bioresorbable and non-bioresorbable are applied directly to the stent surface using spraying, brushing and rolling techniques. The coating can increase the stents biocompatibility and provide a more adhesive stent surface to prevent migration. Furthermore, polymer coating may also have drugs incorporated into the coating to provide the patient with a controlled-release medical device to prevent or treat conditions such as restenosis. Metals and other non-polymers can also be applied to the surface of a medical device. These materials are usually deposited on the device's surface using chemical vapor deposition (CVD) or chemical solution deposition (CSD). However, coatings applied directly to the surface of a polished bare metal device can delaminate; this is especially true for polymers. Delamination can result in unwanted thrombogenic events that may require more aggressive, invasive procedures to correct.

One possible solution that will minimize the aforementioned problems is to provide the implantable medical device with a roughened or textured surface. The elimination of smooth surfaces provides additional surface area for the adhesion of polymers and endothelial cells and provides for superior controlled release of therapeutic agents. Moreover, coatings applied to textured medical devices surfaces are less likely to delaminate.

Textured surfaces enhance controlled drug delivery by providing reservoirs for drugs and thus increase the amount of therapeutic compound that can be loaded onto the device's surface. This in turn increases the time required for physiological fluids to penetrate the device surface and transport the therapeutic compound into the blood stream or adjacent tissue. Recently, titanium provided with textured surfaces has been shown to endothelialize more rapidly and with greater affinity than non-textured titanium surfaces.

Thus, because of the limitations of bare metal medical devices, there remains a need for improved medical devices with textured surfaces.

SUMMARY OF THE INVENTION

The present invention addresses the aforementioned problems by providing implantable medical devices and associated exemplary methods wherein the medical devices have textured surfaces. The textured surfaces of the present invention, as further described with reference to FIGS. 7, 8, 10, 13-17, and 25-29, can be made by any method known to those skilled in the art, for example, and not intended as a limitation, those methods may include a gas-phase plasma, laser etching, acid etching, casting, or mechanical engraving.

In one embodiment of the present invention, a medical device is provided having a textured surface morphology comprising at least one structure selected from the group consisting of cantaloupe (FIG. 8A), brain (FIG. 8B), worms (FIG. 8C) roses (FIG. 8D), a three-dimensionally interconnected porous structure (FIG. 8E), volcanoes (FIG. 17D) and pillars (FIG. 16C). In another embodiment, the textured surface morphology is cantaloupe (FIG. 8A). In another embodiment, the textured surface morphology is brain (FIG. 8B). In another embodiment, the textured surface morphology is worms (FIG. 8C). In another embodiment, the textured surface morphology is roses (FIG. 8D). In another embodiment, the textured surface morphology is a three-dimensionally interconnected porous structure (FIG. 8E). In another embodiment, the textured surface morphology is volcanoes (FIG. 17D). In another embodiment, the textured surface morphology is pillars (FIG. 16C).

In another embodiment, the medical device is selected from the group consisting of neurostimulators, catheters, cardiac valves, shunts, pacemakers, implantable cardioverter defibrillators, stimulation lead tips, medical electrodes, RF ablation devices, vascular stents, stent grafts, drug-delivery devices, catheter tips, bone screws, bone covers, spinal plates, spinal rods and other surgical equipment such as but not limited to tracheal stents, medical prosthesis, feeding tubes, trocar needles, clamps, and forceps.

In another embodiment, the textured surface is provided using a method selected from the group consisting of a gas-phase plasma, laser etching, acid etching, casting, mechanical engraving and combinations thereof. In another embodiment, the medical devices further comprises a coating selected from the group consisting of metals, polymers, oxides, nitrides, carbides, tetraflouroethylene, diamond structures, amorphous carbon structures, poly methylaminomethylstyrene, furanone, silver, quaternary ammonium compounds, dextran, chitosan, glucosamine, hyaluronic acid, hydrogels, heparin, lubricious coatings, silicones, and polysaccharides. In yet another embodiment, the medical device releases at least one bioactive agent selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, bone morphogenic protein, anti-sense nucleotides and transforming nucleic acids.

In one embodiment of the present invention, a method for providing a medical device with a textured surface comprises: placing a medical device in a plasma chamber; reducing the atmospheric pressure within the plasma chamber to provide a process pressure of less than approximately 760 Torr; providing a non-reactive gas to the plasma chamber while maintaining the process pressure of less than approximately 760 Torr; and exposing the medical device to the gas phase plasma to produce a textured surface on the medical device; the textured surface having a morphology selected from the group consisting of cantaloupe (FIG. 8A), brain (FIG. 8B), worms (FIG. 8C) roses (FIG. 8D), a three-dimensionally interconnected porous structure (FIG. 8E), volcanoes (FIG. 17D) and pillars (FIG. 16C).

In one embodiment of the present invention, a method for providing a medical device with a textured surface comprises: placing a medical device in a plasma chamber; reducing the atmospheric pressure within the plasma chamber to provide a process pressure of less than approximately 760 Torr; providing a non-reactive gas to the plasma chamber while maintaining the process pressure of less than approximately 760 Torr; applying sufficient power to a radio frequency (RF) source to generate sufficient RF energy in the plasma chamber to generate a gas-phase plasma; providing at least one additional heat source; and exposing the medical device to the gas phase plasma and the at least one additional heat source to cause a textured surface on the medical device.

In another embodiment, the process pressure ranges from approximately 2 mTorr to approximately 400 mTorr. In another embodiment, the RF frequency comprises frequencies from approximately 10 KHz to approximately 80 MHz. In another embodiment, the non-reactive gas is selected from the group consisting of nitrogen, helium, neon, argon, krypton, xenon and radon. In another embodiment, the non-reactive gas is argon.

In an embodiment, the RF frequency is generated from an RF-biased stage and wherein the RF frequency is continuous, pulsed or any combination thereof. In another embodiment, the applying step further comprises isolating the medical device from the RF frequency source. In another embodiment, the applying step further comprises placing the medical device in direct contact with the RF frequency source. In another embodiment, the power comprises wattages of between approximately 5 W to approximately 5000 W. In another embodiment, the power comprises wattages of between approximately 100 W to approximately 1000 W. In another embodiment, the RF frequency is between approximately 40 KHz and approximately 28 MHz. In another embodiment, the RF frequency is between approximately 2 MHz and approximately 14 MHz. In another embodiment, the process pressure is achieved with non-reactive gas flows of about 2 sccm to about 150 sccm.

In another embodiment of the present invention, the medical device is selected from the group consisting of neuro-stimulators, catheters, cardiac valves, shunts, pacemakers, implantable cardioverter defibrillators, vascular stents, stent grafts, drug-delivery devices, bone screws, bone covers, spinal plates and other surgical equipment such as but not limited to tracheal stents, medical prosthesis, feeding tubes, trocar needles, clamps, and forceps. In another embodiment, the medical device comprises materials selected from the group consisting of stainless steel, MP35N alloy, Pt—Ir, commercially pure titanium (CP Ti), tantalum, nickel titanium alloys, Ti-6Al-4V, cobalt chrome alloys, zirconium, zirconium alloys, molybdenum alloys and combinations thereof.

In an additional embodiment, the at least one additional heat source is provided by RF-field effect, kinetic energy, electromagnetic radiation, induction energy, resistive heat energy or laser energy.

In one embodiment of the present invention, a method for providing a medical device with a textured surface comprises: placing a medical device in a plasma chamber; reducing the atmospheric pressure within the plasma chamber to provide a process pressure of between approximately 100 Torr to approximately $10^{-9}$ Torr; providing a stream of argon gas at between approximately 2 sccm and about 150 sccm to the plasma chamber while maintaining the process pressure of between approximately 100 Torr and approximately $10^{-9}$ Torr; applying between approximately 100 W and approximately 1000 W of power to a radio frequency (RF) source to generate an RF frequency of between approximately 2 MHz and approximately 14 MHz; providing at least one additional heat source; exposing the medical device to the heat source to achieve surface heating; and maintaining the surface heating for a time of between approximately 1 minute and 20 minutes.

In another embodiment, the process pressure is between $10^{-2}$ to $10^{-5}$ Torr. In another embodiment, the RF frequency is 13.56 MHz. In another embodiment, the at least one additional heat source is provided by RF-field effect, kinetic energy, electromagnetic radiation, induction energy, resistive heat energy or laser energy.

In one embodiment of the present invention, a method is provided for texturing medical devices with a combined system of inductively coupled plasma and induction heating comprising: placing a medical device in a plasma chamber; wrapping an induction coil around the medical device; applying power though the induction coil resulting in the heating of the medical device; reducing the atmospheric pressure within the plasma chamber to provide a process pressure of less than approximately 760 Torr; providing a non-reactive gas to the plasma chamber while maintaining the process pressure of less than approximately 760 Torr; and exposing the medical device to the gas phase plasma to produce a textured surface on the medical device.

In another embodiment, the medical device is selected from the group consisting of implantable medical devices, leads, vascular stents, dental wires, dental screws, artificial temporomandibular joints, bone screws, plates, hip prosthesis, bone nails, wires, pins, artificial knee implants, tubular pins, spinal implants, ophthalmic drug delivery devices, ophthalmic rods, surgical tools, dental implants, orthopedic implants and micro-abrasion devices. In another embodiment, the medical device is comprised of a material selected from the group consisting of metals, metal alloys, polymers and ceramics.

In another embodiment of the present invention, the power is applied to the induction coil in alternating current, resulting in a magnetic field. In another embodiment, the power is applied to the induction coil at an alternating current frequency of between approximately 1 kHz and approximately 60 MHz. In another embodiment, the frequency is between approximately 5 kHz and approximately 30 kHz and the surface texturing penetrates the medical device deeply. In another embodiment, the frequency is between approximately 100 kHz and approximately 500 kHz and the surface texturing penetrates the medical device shallowly. In another embodiment, the frequency is between approximately 400 kHz and approximately 60 MHz and the medical device is very small. In another embodiment, the induction heating and plasma generation systems each have their own RF power supply. In another embodiment, each RF power supply generates a different RF frequency.

In one embodiment of the present invention, a medical device is provided having a surface texture made by a method according to any of the methods disclosed herein. In another embodiment, the medical device has a surface texture morphology comprising at least one structure selected from the group consisting of cantaloupe (FIG. 8A), brain (FIG. 8B), worms (FIG. 8C) roses (FIG. 8D), a three-dimensionally interconnected porous structure (FIG. 8E), volcanoes (FIG. 17D) and pillars (FIG. 16C). In another embodiment, the pillar structure morphology is selected from at least one of FIG. 16B, FIG. 16B, FIG. 25A, and FIG. 26A. In another embodiment, the rose structure morphology is selected from at least one of FIG. 8D, FIG. 28A, and FIG. 28B. In another embodiment, the three-dimensionally interconnected porous structure morphology is selected from at least one of FIG. 8E, FIG. 25D and FIG. 27B. In another embodiment, the worm structure morphology is selected from at least one of FIG. 8C and FIG. 30.

In one embodiment of the present invention, a medical device having a textured surface formed thereon is provided wherein the textured surface comprises a plurality of protrusions extending from the medical device surface wherein the protrusions have a diameter between about 0.05 μm and about 0.40 μm, a height between about 1 μm and 2 μm and a density of protrusions between about 3 μm$^2$ and about 30 μm$^2$.

In one embodiment of the present invention, a medical device having a textured surface formed thereon is provided wherein the textured surface comprises a plurality of protrusions forming a three dimensionally interconnected porous web extending from the medical device surface wherein pores associated with the three dimensionally interconnected porous web have a diameter between about 0.05 μm and about 4.5 μm and a pore density between about 0.3/μm$^2$ and about 0.8/μm$^2$, the three dimensionally interconnected porous web has a height between about 2 μm and about 4 μm and an aspect ratio of between about 10 and about 12.

In one embodiment of the present invention, a medical device having a texture surface formed thereon is provided wherein the textured surface comprises interwoven leaflets formed into a rose morphology wherein the height of the roses is about 0.2 μm to about 2.2 μm, the density of the roses is between about 0.5/μm$^2$ and about 1.5/μm$^2$, the diameter of the roses is between about 1.0 μm and about 2.5 μm and the leaflet width is between about 0.08 μm and about 0.2 μm.

BRIEF DESCRIPTION OF THE DRAWINGS

FIG. 1 depicts a process chamber comprising a gas inlet nozzle, a platform, holes in the platform for placement of posts, posts and the structure of the radio frequency (RF)-biased electrodes in accordance with the teachings of the present invention.

FIG. 2 depicts a medical device positioned on the sample platform/electrode in various vertical configurations in accordance with the teachings of the present invention.

FIG. 3 depicts a medical device positioned on the sample platform/electrode in various horizontal configurations in accordance with the teachings of the present invention.

FIGS. 7B-D depict the surface morphology at time points between 5 seconds and 600 seconds.

FIGS. 10B-10D depict the surface morphology of rings between ring 1 and ring 15.

FIG. 16B depicts the surface morphology at a time point between 2 minutes and 10 minutes.

FIG. 17C is a higher magnification (×10,000) of FIG. 17B (×5,000). FIG. 17D is a tilted angle view of the texture morphology of FIG. 17C.

FIGS. 22A and 22B are not drawn to the same scale.

FIG. 24A-B schematically illustrates an elevated perspective view (FIG. 24A) and a cross-section view (FIG. 24B) of a portion of an embodiment of a medical device surface having 'worm' morphology according to the teachings of the present invention.

FIG. 28C depicts a cross-section of a 'rose' morphology textured substrate.

FIG. 30A-B depicts the durability of a polymer coating on a bare metal stent (FIG. 30A) and a textured stent (FIG. 30B) according to the teachings of the present invention.

DEFINITION OF TERMS

Figure 4:
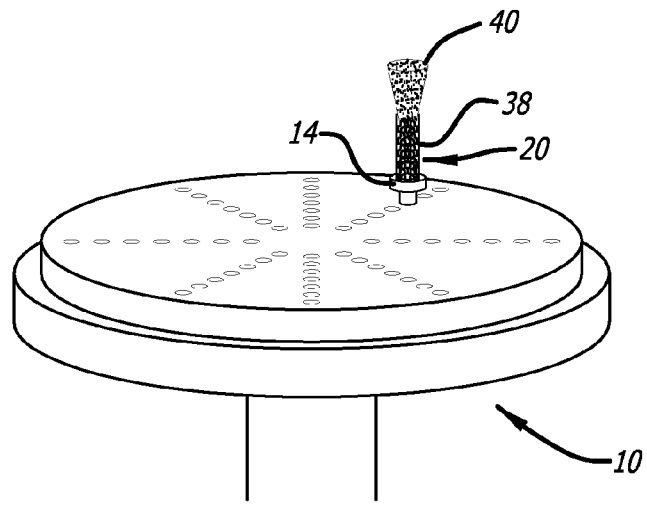
FIG. 4 depicts the sample platform/electrode comprising a post on which a stent is placed, a secondary plasma generated by the stent and a glow associated with surface heating of the stent in accordance with the teachings of the present invention.

Generally, all technical terms or phrases appearing herein are used as one skilled in the art would understand to be their ordinary meaning. However, for the convenience of the reader selected terms are more specifically defined as follows.

Bioactive Agent: As used herein, "bioactive agent" shall include any compound or drug having a therapeutic effect in an animal. Exemplary, non limiting examples include anti-proliferatives including, but not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, and nucleic acids including anti-sense nucleotides and transforming nucleic acids. Drugs can also refer to bioactive agents including, cytotoxic and cytostatic compounds, toxic compounds, chemotherapeutic agents, analgesics, antibiotics, statins, polypeptides, growth factors, delivery vectors including recombinant micro-organisms, liposomes, matrix metalloproteinase inhibitors, anti-angiogenic factors, steroids, nonsteroidal anti-inflammatory agents, corticosteroids, prostaglandin receptor antagonists, platelet activating factor receptor antagonists, antiviral agents, antifungal agents, anti-protozoan agents, antineoplastic angiogenic factors, calcium channel blockers, thrombolytic agents, angiotensin converting enzyme inhibitors, antihypertensive agents, anti-coagulants, antiarrhythmic agents, agents to treat congestive heart failure, cholesterol lowering drugs, anti-psychotics, and the like.

Exemplary FKBP-12 binding agents include sirolimus (rapamycin), tacrolimus (FK506), everolimus (certican or RAD-001), temsirolimus (CCI-779 or amorphous rapamycin 42-ester with 3-hydroxy-2-(hydroxymethyl)-2-methylpropionic acid as disclosed in U.S. patent application Ser. No. 10/930,487) and zotarolimus (ABT-578; see U.S. Pat. Nos. 6,015,815 and 6,329,386). Additionally, other rapamycin hydroxyesters as disclosed in U.S. Pat. No. 5,362,718 may be used in combination with the polymers of the present invention.

Inert Gas: As used herein an "inert gas" refers to a noble gas including the chemical elements in group 18 (old-style Group 0) of the periodic table. This chemical series contains helium, neon, argon, krypton, xenon and radon.

Glow: As used herein "glow" refers to a physical state of a substrate exposed to the plasma of the present invention such that the surface is heated to the point where the surface becomes incandescent. Surface glowing is not necessary for texturing to occur, but may be useful as an empirical indicator of process progression and surface heating Heating Means: As used herein, "heating means" is defined as an energy source that heats the surface of a medical device in accordance with the teachings of the present invention such that, when used in combination with a gas-phase plasma, a texturing temperature is reached. Non-limiting examples of heating means include without limitation, RF-field effect, kinetic energy, electromagnetic radiation, induction energy, resistive heat energy and laser energy. Thus any device used to provide heat using RF-field effect, kinetic energy, electromagnetic radiation, induction energy, resistive heat energy and laser energy is considered a "heating means" as used herein and is considered within the scope of the present invention.

Morphology: As used herein, "morphology" refers to the microgeometry, shape and form of the surface texture formed on a substrate using the methods disclosed herein.

Non-reactive Gas: As used herein "non-reactive" gas includes all noble gases and additionally includes molecular nitrogen.

Plasma or gas-phase plasma: As used herein "plasma" refers to an ionized gas. "Ionized" means that at least one electron has been removed from a significant fraction of the molecules. The ionized gas contains free ions and electrons, and therefore is electrically conductive. A plasma also contains other excited species, such as free radicals and photons.

Process pressure: As used herein, "process pressure" refers to the plasma reactor chamber pressure while texturing as measured in Torr. Generally, process pressure is less than standard atmospheric pressure, that is at least a partial vacuum is present in the chamber (less than normal atmospheric pressure, 760 Torr or 14.7 psi). However, process pressures may be greater than 760 Torr.

Substrate: As used herein "substrate" refers to any surface to be surface textured.

Surface heating: As used herein, "surface heating" refers to processes that heats a medical device's surface to the point where texturing begins. Specifically, the term "surface heating" refers to a process whereby the surface of a medical device is heated to texturing temperature using a gas-phase plasma and at least one additional heating means such that the resulting texturing temperature exceeds the temperature that can be reached on a medical device surface using a gas-phase plasma alone.

Texturing: As used herein "texturing" describes the physical process of altering the surface of a medical device to provide a three dimensional structure of varying complexity. Methods useful in accordance with the teachings of the present invention include, without limitation, bombarding a medical device surface with gas-phase plasma ions such that surface erosion occurs, resulting in a textured surface, Other means for achieving the textures depicted in the figures of the present invention may include laser etching, acid etching, casting, and mechanical engraving. Surface erosion may or may not be associated with elemental compositional changes.

Texturing temperature: As used herein, "texturing temperature" refers to the temperature as measured on a medical device's surface at the point where texturing begins. Texturing temperature may or may not be associated with surface glow.

DETAILED DESCRIPTION OF THE INVENTION

The present invention provides implantable medical devices and associated methods wherein the medical devices have textured surfaces. The textured surfaces of the present invention, as further described with reference to the figures, can be made by any method known to those skilled in the art, for example, and not intended as a limitation, those methods may include a gas-phase plasma, laser etching, acid etching, casting, or mechanical engraving.

Specifically, the present invention provides implantable medical devices comprised of metals, polymers and ceramics having surfaces with textured morphology. Moreover, the surfaces of the implantable medical devices may be further coated with polymers, metals and other materials such as, but not limited to, ceramics. The textured surfaces are also receptive to deposition of materials from gases such as, but not limited to, methane, and ammonia. Furthermore, metals and organic residues such as, but not limited to, metal alkoxides, metal carboxylates and metal diketonates may be surface deposited on the medical device. The textured surfaces of the medical devices of the present invention provide advantageous morphologies that promote cell growth, provide means for the controlled delivery of bioactive agents to adjacent anatomical sites, improve surface coating adherence and promote tissue ingrowth allowing for superior medical device in situ position retention.

The implantable medical devices of the present invention include, but are not limited to, neurostimulators, catheters, cardiac valves, shunts, pacemakers, implantable cardioverter defibrillators, stimulation lead tips, medical electrodes, RF ablation devices, stents, stent grafts, drug-delivery devices, catheter tips, bone screws, bone covers, spinal plates, spinal rods, medical prosthesis, feeding tubes, trocar needles, clamps, forceps, guidewires, tissue cutting tools, vein harvesting tools, needles, lead anchors, fixation devices and the like. The texturing methods of the present invention can be used in all dental applications, such as but not limited to dental screws, dental wires, dental implants, artificial temporomandibular joint replacements, and the like. Further medical devices that can be effectively textured using the methods of the present invention including, but are not limited to, ophthalmic drug delivery devices, micro-abrasion devices, orthopedic implants, dental implants, dental wires, and surgical tools that require rough surfaces or non-slip surfaces. Ophthalmic drug delivery devices include, but are not limited to, ophthalmic rods. Ophthalmic rods are drug delivery devices for ophthalmic medications, and are typically long rods coated with an ocular diagnostic or therapeutic agent. The micro-abrasion devices are used in dental applications such as, but not limited to, tooth surfacing or surgical procedures such as, but not limited to, tissue roughening. Orthopedic implants include, but are not limited to, bone screws, plates, hip prosthesis, bone nails, wires, pins, artificial knee implants, tubular pins, and spinal implants. Advantages offered by the texturing of implantable medical devices include better tissue-implant contact due to the increased surface area resulting from the texturing. The result is better bond in-growth that allows for a higher pull out force.

The textured medical device of the present invention may be made using many different techniques. As an exemplary method, and not intended as a limitation, medical device surfaces are textured by placing the medical device in a gas-phase plasma chamber and applying sufficient thermal energy to the device surface to cause the device's surface to reach texturing temperature. In one embodiment of the present invention, a medical device is surface heated in a gas-phase plasma chamber using an inert gas-phase plasma and optionally with at least one additional energy source, such that surface heating is achieved. Gas-phase plasma is an electrically conductive gas containing charged particles. When RF-energy exposure excites gas atoms within a reduced atmosphere chamber, outer orbital electrons become ionized producing plasma containing a mixture of electrons, ions, radicals, photons, recombination products and neutrals.

There are several factors that affect the plasma efficiency and thus its affect on a substrate surface. One factor is the source gas used to generate the plasma. Examples of suitable non-reactive gases include, but are not limited to, molecular nitrogen and the six noble (inert) gases including helium, neon, argon, krypton, xenon, and radon, any one of which can be used as the primary plasma gas. Argon is probably the most favored primary plasma gas and in some industrial applications such as surface cleaning and etching, may be used with a secondary plasma gas such as hydrogen, helium or nitrogen to increase its effectiveness. Argon forms a plasma readily and tends to be less aggressive towards chamber electrodes and substrates; most mixed gas plasmas are ignited using pure argon. Electrode spacing and size, roughness of electrodes or reactor walls, patterning of electrodes, size of reactor, reactor load, substrate placement and electrode charging are additional parameters that may affect plasma system performance.

The substrate temperature during texturing impacts several factors that can either enhance or negatively affect the desired results. Characteristics such as sputter rate, selectivity, morphology and uniformity can reflect small changes in substrate temperature. Higher temperatures can enhance sputtering but may also cause surface roughness and more isotropic removal of material (non-directional removal of material from a substrate via a physical process). Control of substrate temperature can be achieved by operating the plasma at lower power or lower pressure. At increased power, plasma ion substrate bombardment increases, causing the substrate surface to heat and eventually glow. At lower pressures, the coefficient of heat transfer is decreased. Conversely if higher temperatures are desired, higher power and increased pressure are needed to increase substrate heat to the glow point. Another factor affecting substrate heating is the presence of heat sinks in the chamber. Heat sinks can include fixtures for attaching the substrate to the chamber platform such as electrodes. Heat sinks can also include electrodes. A substrate surface in direct contact with the attachment fixture will have lower surface temperatures than substrate surfaces not in contact with, or farther away from, the fixture. A heat sink is any material capable of absorbing heat or thermal energy away from the substrate. However, there remains an absolute maximum substrate surface temperature that can be achieved using a gas-phase plasma alone and this maximum substrate surface temperature may not provide the full range of textures within the scope of the present invention.

Thus, the present inventors have surprisingly discovered a method that provides a controllable process whereby medical device surfaces can be provided with an elaborate array of diverse surface textures. Exemplary surface texture morphologies are depicted in FIGS. 7, 8, 10, 13-17, and 25-29. The surface textures provided by the present invention are typified by distinct protrusions on a surface of a substrate. The methods of the present invention produce surface textures that can be uniform or non-uniform. If non-uniform, the surface texture is nonetheless characterized by a deliberate array of surface features. Therefore, whether the features are uniform or non-uniform, they are not random. Surface texture morphologies provided by the present invention can, but not need, have a directionality associated with either or both of parallel or perpendicular to the longitudinal axis of the substrate.

The morphologies are defined based on the dimensional aspects of protrusions, troughs, pores and bridges formed on the surface of the substrate. Individual morphologies can be further defined by the mean value of the width and depth of the troughs, width and height of the protrusions, presence, absence or size of pores or bridges. The protrusions can be of any shape, rounded, flat-topped, angular or irregularly shaped. Additionally, the morphologies can be defined by the mean value of the spacing between the protrusions or troughs. The dimensional aspects of the morphology are controlled by one or more of the process parameters of the surface texturing process of the present invention.

The present inventors refer to the individual morphologies using descriptive terms and have classified them into four non-limiting morphological categories.

Group 1 comprises morphologies having a plurality of randomly oriented protrusions extending outward from the substrate surface to a substantially constant height. The troughs between the protrusions are of substantially constant depth. Group 1 includes morphologies depicted in scanning electron micrographs and referred to as 'pillars' (FIGS. 16, 25A and 26), 'brain' (FIGS. 8B and 25B), 'cantaloupe' (FIGS. 8A and 25C) and 'three dimensional interconnecting porous structure' (FIGS. 8E, 25D and 27).

Figure 18A:
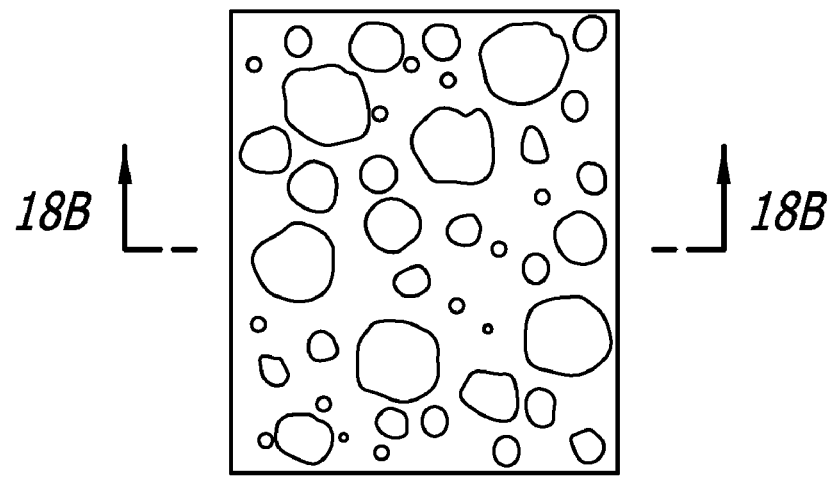
FIG. 18A-B schematically illustrates an elevated perspective view (FIG. 18A) and a cross-section view (FIG. 18B) of a portion of an embodiment of a medical device surface having 'pillar' morphology according to the teachings of the present invention.
Figure 18B:
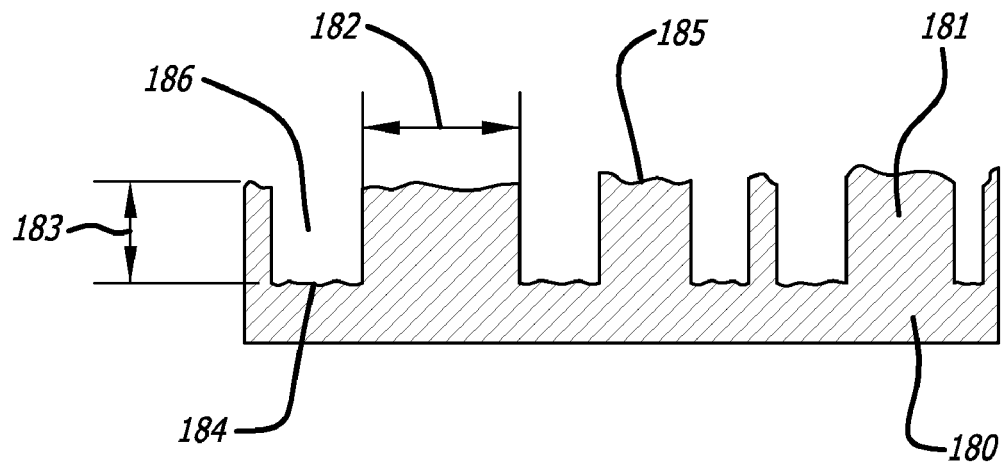

The pillar morphology is schematically depicted in FIG. 18 from a top view (FIG. 18A) and a cross-section view (FIG. 18B) and is characterized by substantially parallel protrusions 181 (pillars) extending substantially perpendicular to the substrate surface 180. In the pillar morphology, the number density average (the number of pillars per $\mu m^2$) is between about $3/\mu m^2$ and $30/\mu m^2$. In one embodiment, the average density of pillars 181 is $12.9/\mu m^2$. The diameter 182 of the pillars 181 ranges from about 0.05 µm to about 0.40 µm. A substrate surface 180 having pillar morphology typically contains protrusions 181 having many different diameter sizes. In one embodiment, the average diameter 182 of the pillars is 0.2 µm. The height 183 of the pillars 181 ranges from about 1 µm to about 2 µm measured from the base of the trough 186 to the peak 185 of pillar 181.

Figure 19A:
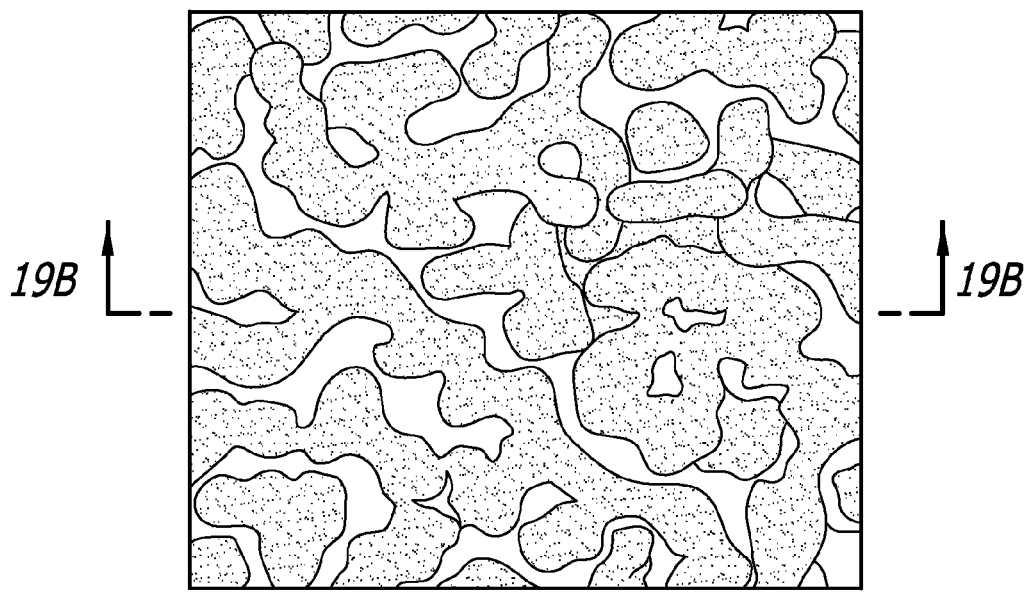
FIG. 19A-B schematically illustrates an elevated perspective view (FIG. 19A) and a cross-section view (FIG. 19B) of a portion of an embodiment of a medical device surface having 'brain' morphology according to the teachings of the present invention.
Figure 19B:
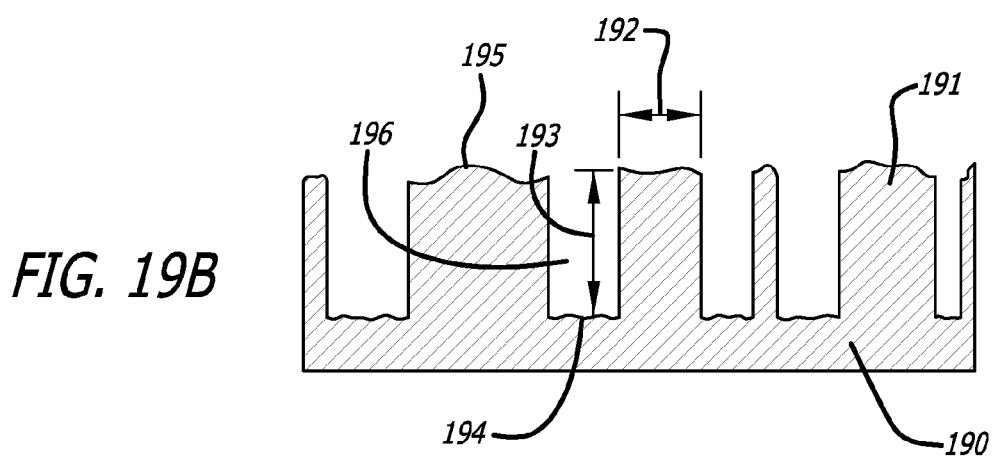
Figure 19C:
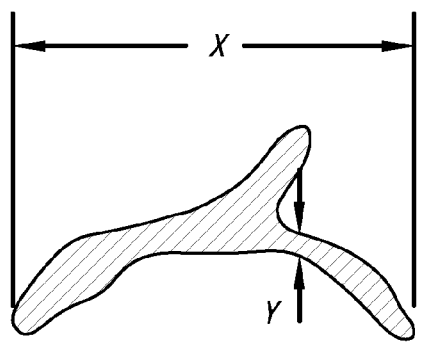

As the surface texture becomes more complex, 'brain' morphology is formed. The brain morphology is schematically depicted in FIG. 19 from a top view (FIG. 19A) and a cross-section view (FIG. 19B). Brain morphology is characterized by substantially parallel protrusions 191 substantially perpendicular to the substrate surface 190. The protrusions of the brain morphology are taller (greater height), wider (greater diameter) and have a lower number density than the pillar morphology. In the brain morphology, the number density average of protrusions is between about $0.7/\mu m^2$ and $1.5/\mu m^2$. In one embodiment, the average density of protrusions is $1.2/\mu m^2$. The diameter 192 of the protrusions 191 ranges from about 0.1 µm to about 9.0 µm. A substrate surface 190 having brain morphology typically contains protrusions 191 having many different diameter sizes. In one embodiment, the average diameter 192 of the pillars is 1.2 µm. The height 193 of the protrusions 191 ranges from about 2 µm to about 3 µm measured from the base 194 of the trough 196 to the peak 195 of protrusion 191. Furthermore, the aspect ratio (the ratio between the length of the major axis x and the minor axis y of the elongated microstructural features) of the brain morphology is between about 20 and about 25. The major axis is the axis along the longest distance from one end to another of a brain microstructure and the minor axis is perpendicular to the major axis. The minor axis length is the shortest distance of a brain microstructure along the minor axis.

Figure 20A:
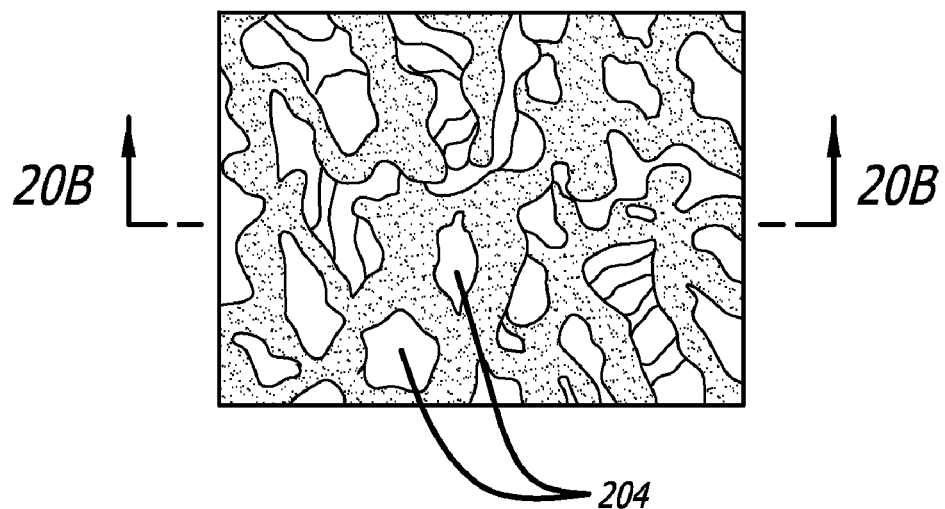
FIG. 20A-B schematically illustrates an elevated perspective view (FIG. 20A) and a cross-section view (FIG. 20B) of a portion of an embodiment of a medical device surface having 'cantaloupe' morphology according to the teachings of the present invention.
Figure 20B:
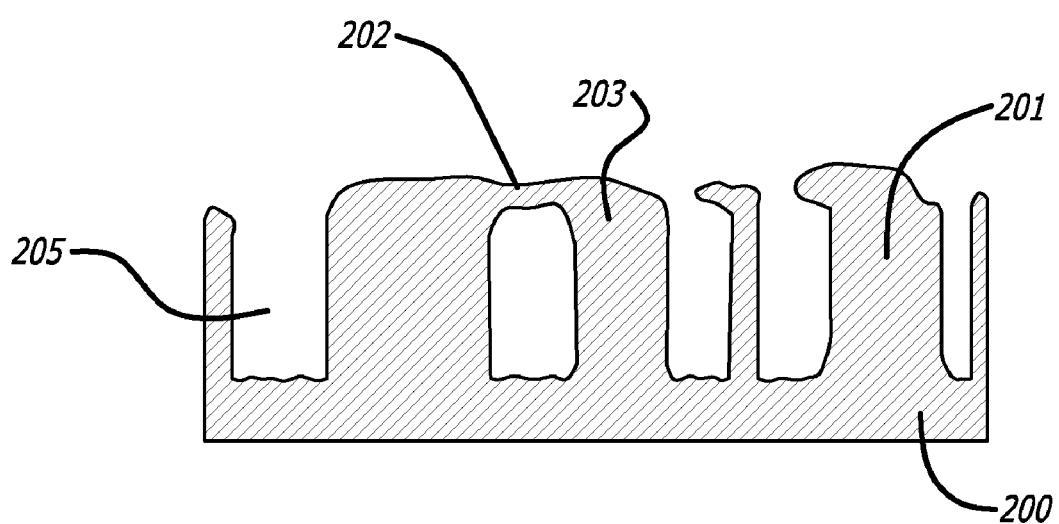

As the surface texture becomes yet more complex, 'cantaloupe' morphology is formed. The cantaloupe morphology is schematically depicted in FIG. 20 from a top view (FIG. 20A) and a cross-section view (FIG. 20B). Cantaloupe morphology is characterized by substantially parallel protrusions 201 substantially perpendicular to the substrate surface 200 that form an interconnected web 202 at the top surface 203 of the protrusions 201. The interconnected web has a loose formation with pores 204 and the shape of trough 205 is substantially the same as the trough formed in the pillar and brain formations. In the cantaloupe morphology, the number density average, the protrusion diameter and height are substantially similar to those found in the brain morphology.

Figure 21A:
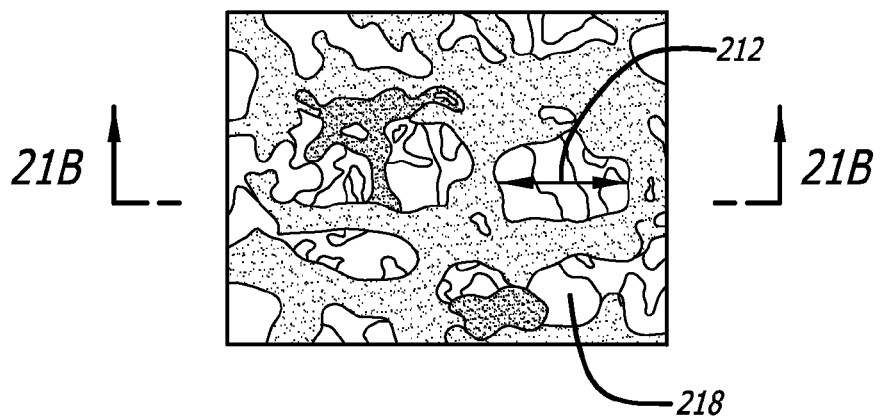
FIG. 21A-B schematically illustrates an elevated perspective view (FIG. 21A) and a cross-section view (FIG. 21B) of a portion of an embodiment of a medical device surface having three-dimensional interconnected porous structure morphology according to the teachings of the present invention.
Figure 21B:
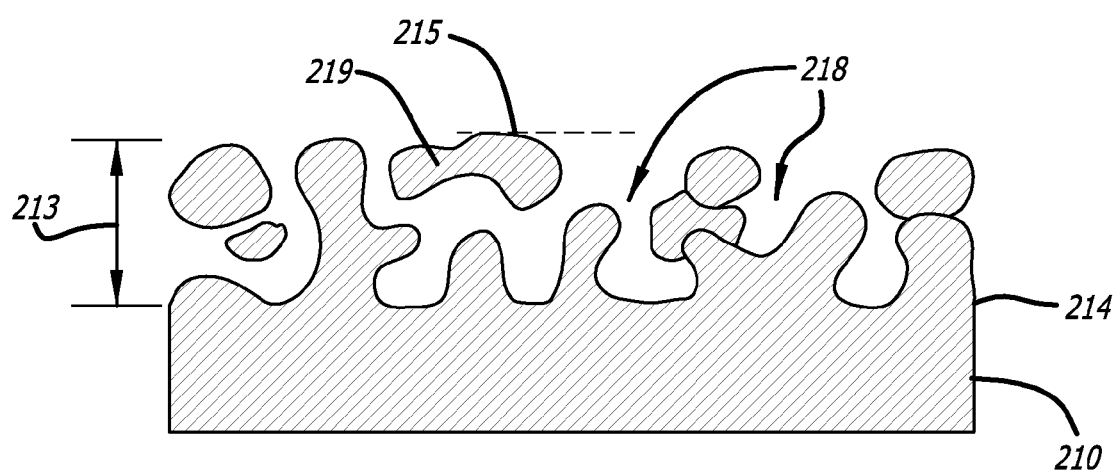

The most complex surface texture in Group 1 is the three-dimensional interconnected porous structure (3D structure). The 3D structure morphology is schematically depicted in FIG. 21 from a top view (FIG. 21A) and a cross-section view (FIG. 21B). The 3D structure morphology is characterized by protrusions 211 from the substrate surface 210 which can become smaller segments and form a three-dimensionally interconnected porous web 219. Pores 218 are formed within the three-dimensionally interconnected porous textured portion of the substrate surface 210. In the 3D structure morphology, the number density average of the pores 218 are between about $0.3/\mu m^2$ and $0.8/\mu m^2$. In one embodiment, the average density of the pores 218 in the 3D structure is $0.6/\mu m^2$. The diameter 212 of the pores 218 ranges from about 0.5 μm to about 4.5 μm. A substrate surface 210 having 3D structure morphology typically contains pores 218 having many different diameter sizes. In one embodiment, the average diameter 212 of the pores 218 is 1.3 μm. The height 213 of the 3D structure ranges from about 2 μm to about 4 μm measured from the base 214 of the trough 216 to the top 215 of interconnected web 219. Furthermore, the aspect ratio of the 3D structure morphology is between about 10 and about 12.

Figure 22A:
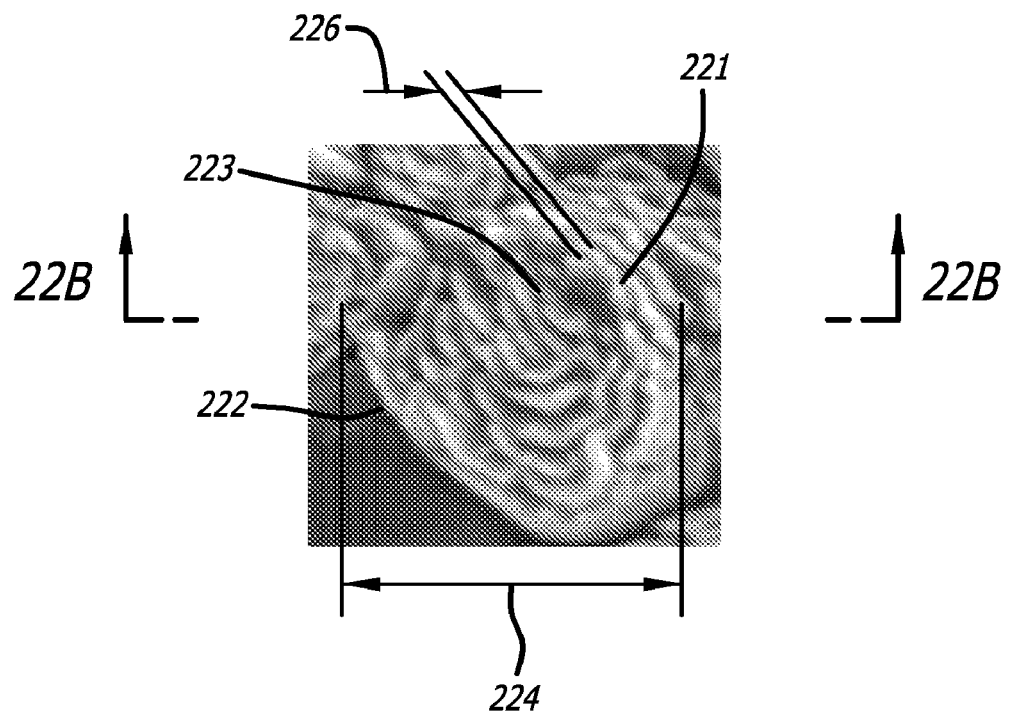
FIG. 22A-B schematically illustrates an elevated perspective view (FIG. 22A) and a cross-section view (FIG. 22B) of a portion of an embodiment of a medical device surface having 'rose' morphology according to the teachings of the present invention.
Figure 22B:
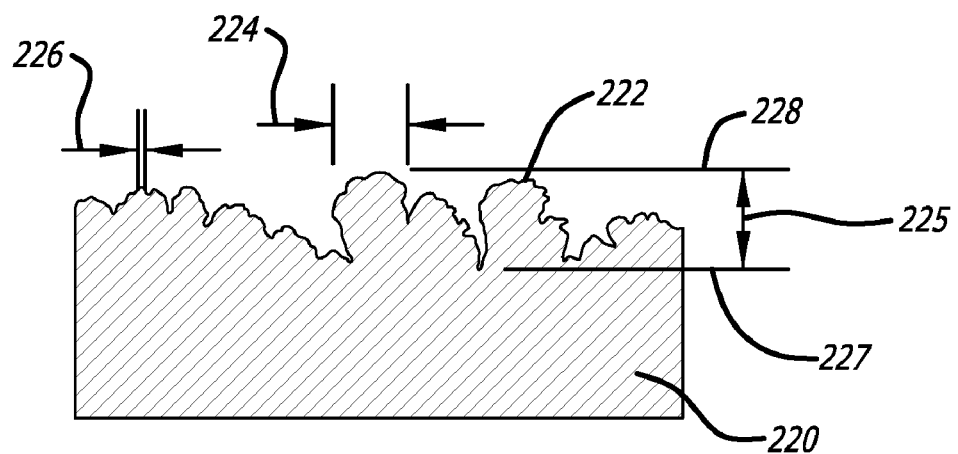

Scanning electron micrographs of the second type of surface texture morphology (Group 2), 'rose' morphology, formed on platinum-iridium alloy substrates are found in FIGS. 8D and 28A-C. The rose morphology is schematically depicted in FIG. 22 from a top view (FIG. 22A) and a cross-section view (FIG. 22B). The rose morphology comprises a plurality of individual rose structures 221 formed on the substrate surface 220. Each rose structure 221 has interwoven leaflets 222 radiating from a central point 223, resembling the petals of a rose. In the rose morphology, the number density average of roses 221 is between about $0.5/\mu m^2$ and $1.5/\mu m^2$. In one embodiment, the average density of roses 221 is $0.9/\mu m^2$. The diameter 224 of the roses 221 ranges from about 1.0 μm to about 2.5 μm. A substrate surface 220 having rose morphology typically contains roses 221 having many different diameter sizes. In one embodiment, the average diameter 224 of the roses 221 is about 1.7 μm. The leaflet thickness 226 ranges from approximately 0.08 μm to approximately 0.2 μm. In one embodiment, the leaflet thickness 226 is approximately 0.13 μm. The height 225 of the roses 221 ranges from about 0.2 μm to about 2.2 μm measured from the base 227 of the rose 221 to the peak 228 of rose 221. In one embodiment, the average height 225 of the roses 221 is about 1.4 μm.

Figure 23A:
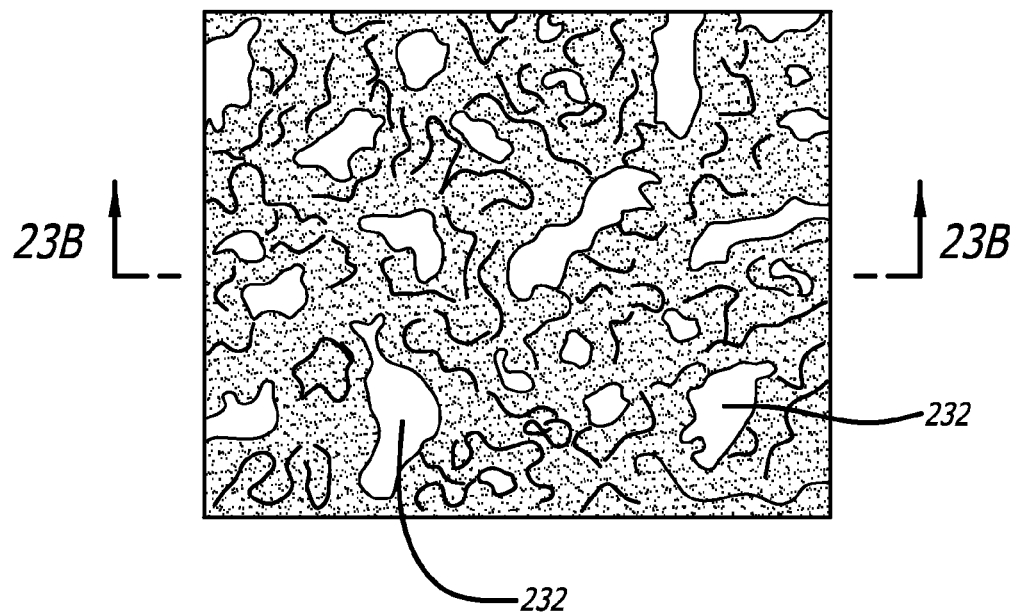
FIG. 23A-B schematically illustrates an elevated perspective view (FIG. 23A) and a cross-section view (FIG. 23B) of a portion of an embodiment of a medical device surface having 'volcano' morphology according to the teachings of the present invention.
Figure 23B:
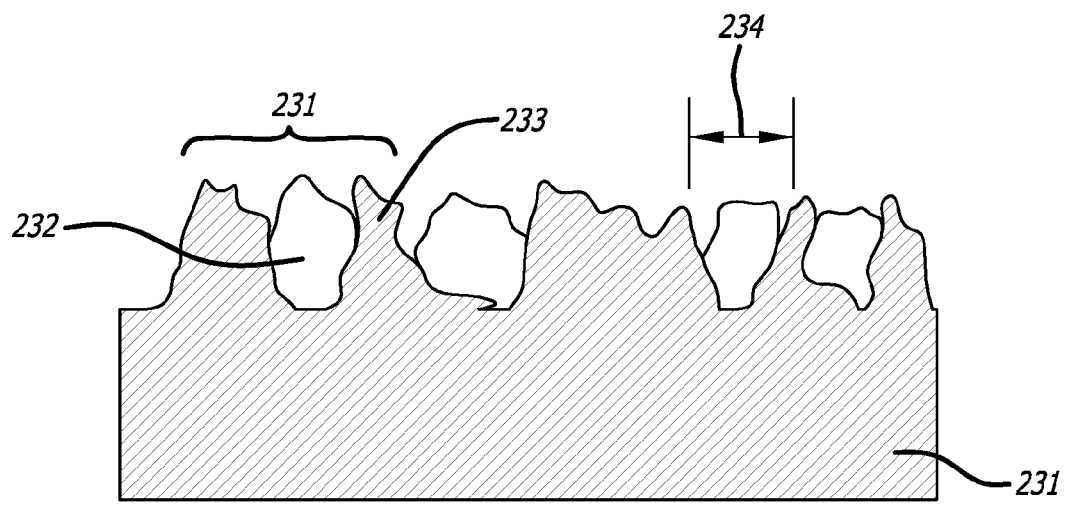

The third type of surface texture morphology (Group 3) comprises the 'volcano' morphology. Scanning electron micrographs of the volcano morphology formed on Ti-6Al-4V alloy substrates are found in FIG. 17B-D. The volcano morphology is schematically depicted in FIG. 23 from a top view (FIG. 23A) and a cross-section view (FIG. 23B). The volcanoes 231 comprise roughly cone-shaped, oblong crater-like pores 232 surrounded by protrusions 233 rising from the substrate surface 230. In the volcano morphology, the number density average of pores 232 is between about $1.5/\mu m^2$ and about $3.0/\mu m^2$. In one embodiment, the average density of pores 232 is $2.3/\mu m^2$. The pore diameter 234 of the volcanoes structures ranges from about 0.02 μm to about 3.7 μm. A substrate surface having volcano morphology typically contains pores having many different diameter sizes. In one embodiment, the average pore diameter 234 of the volcanoes is about 0.29 μm. The aspect ratio of the volcano morphology ranges from about 14 to about 15.

The fourth type of surface texture morphology (Group 4), comprises a morphology from any of Groups 1-3 having a further deposition from a secondary plasma. The present inventors have referred to the Group 4 morphology as 'worm' morphology. Scanning electron micrographs of the worm morphology are found in FIGS. 8C and 29. The worm morphology is schematically depicted in FIG. 24 from a top view (FIG. 24A) and a cross-section view (FIG. 24B). In one exemplary embodiment, the secondary plasma forms a carbon coating on the substrate material. In one embodiment, the worm morphology is characterized by protrusions 241 on the substrate surface 240 and an interconnected web 242 at the top surface of the protrusions 241 of the carbon coating forming interconnected worm-like structures 243. In the worm morphology, the number density average of protrusions 241 is between about $3/\mu m^2$ and $30/\mu m^2$. The width 248 of the worms 243 ranges from about 0.05 μm to about 1.5 μm. A substrate surface 240 having worm morphology typically contains interconnected worms 243 having many different widths. The height 245 of the worm surface texture ranges from about 1 μm to about 3 μm as measured from the base 246 of the protrusions 241 to the highest point 247 of the secondary deposition forming the interconnecting web 242.

As used herein the term "surface heating" refers to processes that heats a medical device's surface to the point where texturing begins. Specifically, the term "surface heating" refers to a process whereby the surface of a medical device is heated to texturing temperature using a gas-phase plasma and at least one additional heating means such that the resulting texturing temperature exceeds the temperature that can be reached on the substrate surface using a gas-phase plasma alone. Surface heating, as used herein, is achieved by controlling non-reactive gas selection, energy source output, chamber pressure, electrode design, fixture design, substrate position relative the electrodes and process time, and the use of at least one additional heating means.

Generally, the process of the present invention includes, but is not limited to, (1) placing a medical device to be processed within a plasma reactor chamber; (2) evacuating a plasma reactor to provide a process pressure of less than 760 Torr, (3) providing a stream of at least one non-reactive gas to the chamber while maintaining a process pressure of less than 760 Torr; (3) supplying RF energy from an RF energy source at a level and frequency sufficient to initiate a gas phase plasma comprised essentially of the at least one non-reactive gas ions; (4) adjusting chamber pressure and power levels; and (5) using at least one additional heating means to achieve surface heating. Thus, according to the teachings of the present invention, this process textures the surfaces of medical devices placed within the plasma chamber resulting in complex three dimensional surfaces.

In one embodiment of the present invention, the implantable medical devices are placed in an RF-biased vacuum chamber as depicted in FIG. 1. The RF-biased vacuum chamber 11 comprises at least one electrode, preferably multiple electrodes. In one embodiment, the chamber comprises a first electrode 10, which can also serve as a sample platform and may include the sample itself. The chamber is evacuated and a stream of non-reactive gas such as, but not limited to, argon, is introduced with a constant or fluctuating vacuum being drawn. An operating pressure, or process pressure, is maintained at between approximately $10^{-10}$ Torr to 100 Torr. The at least one electrode, or multiplicity of electrodes, are biased with RF frequencies between approximately 10 kHz to 80 MHz using an RF signal generator and RF power amplifier (not shown in FIG. 1) operating at between approximately 5 to 5,000 watts. An RF generator can alternately be operated at voltages between approximately 50 to 2,000 volts. The precise operational parameters associate with vacuum chamber RF-biased plasma cells are known to those skilled in the art (see for example, E. C. Benck, A. Schwabedissen, A. Gates, and J. R. Roberts. J. Vac. Sci. Technology. A(16)1 Jan/Feb 1998 306-315; U.S. Pat. No. 6,481,370 B2 issued Nov. 19, 2002 to Kazumi et al. both of which are incorporated herein by reference for all they teach regarding the operation or function of vacuum chamber RF-biased plasma cells.)

The medical device to be processed according to the teachings of the present invention can be positioned within the chamber 11 in various configurations as depicted in FIGS. 2 and 3. FIG. 2 depicts the placement of a medical device 20 on the electrode platform 10 such that the medical device is placed in a vertical position. In one embodiment, medical device 20 is placed on a support pillar 14. Alternatively the medical device can be placed directly on the platform's 10 surface as shown at 20A. Additionally, medical device 20 can be suspended between two support rods 22 by a wire 24. Support pillar 14 and rods 22 can be either electrically conductive or non-conductive. If the support pillar 14 or rods 22 are electrically conductive, the sample 20 also functions as an electrode which may increase surface heating. In another embodiment, the support pillar 14 or rods 22 are electrically non-conductive and thus the sample 20 is insulated from the electrode platform 10 resulting in potentially less surface heating relative to a sample 20 that also acts as electrode. The differences in surface heating may affect surface texturing and thus provides an additional means for controlling surface heating and sample 20 surface texture morphology. In one embodiment of the present invention the additional heating means required to achieve surface heating is provided by RF field effect.

FIG. 3 depicts various means for placing the medical device 20 on the platform 10 such that the medical device is placed in a horizontal position. In one embodiment, medical device 20B is placed horizontally between two support rods 22 over a horizontal brace 28. In another configuration medical device 20C may be attached at the end of support brace 28 such that it is disposed partially between the vertical and horizontal position. Further, medical device 20D may be placed directly on the platform's 10 surface. In yet another configuration, medical device 32 can be attached directly to support rod 22 without the use of support brace 28. Of course it is understood by those skilled in the art that the preceding placement configurations are non-limiting and represent only a few of the myriad placement configurations. The exact placement configuration will be determined by the type of medical device to be processed and the type of texture desired. In the preceding examples the medical device 20 is a vascular stent and the medical device 32 is a coil, screw or medical electrode. In one embodiment of the present invention, a 12 mm vascular stent 20 is exposed to the texturing process. In another embodiment, a 18 mm stent 20 is exposed to the texturing process. In other embodiments, stent 20 lengths vary from, but are not limited to, 2 mm to 50 mm.

In another embodiment of the present invention, the texturing process can be controlled by adjusting process pressure and non-reactive gas flow. In one embodiment, a constant flow of argon in the chamber is regulated by a mass flow controller. In another embodiment of the present invention, the argon flow is regulated manually. In still another embodiment, the vacuum being drawn in the chamber is held constant. In another embodiment, the vacuum being drawn in the chamber fluctuates.

Figure 5:
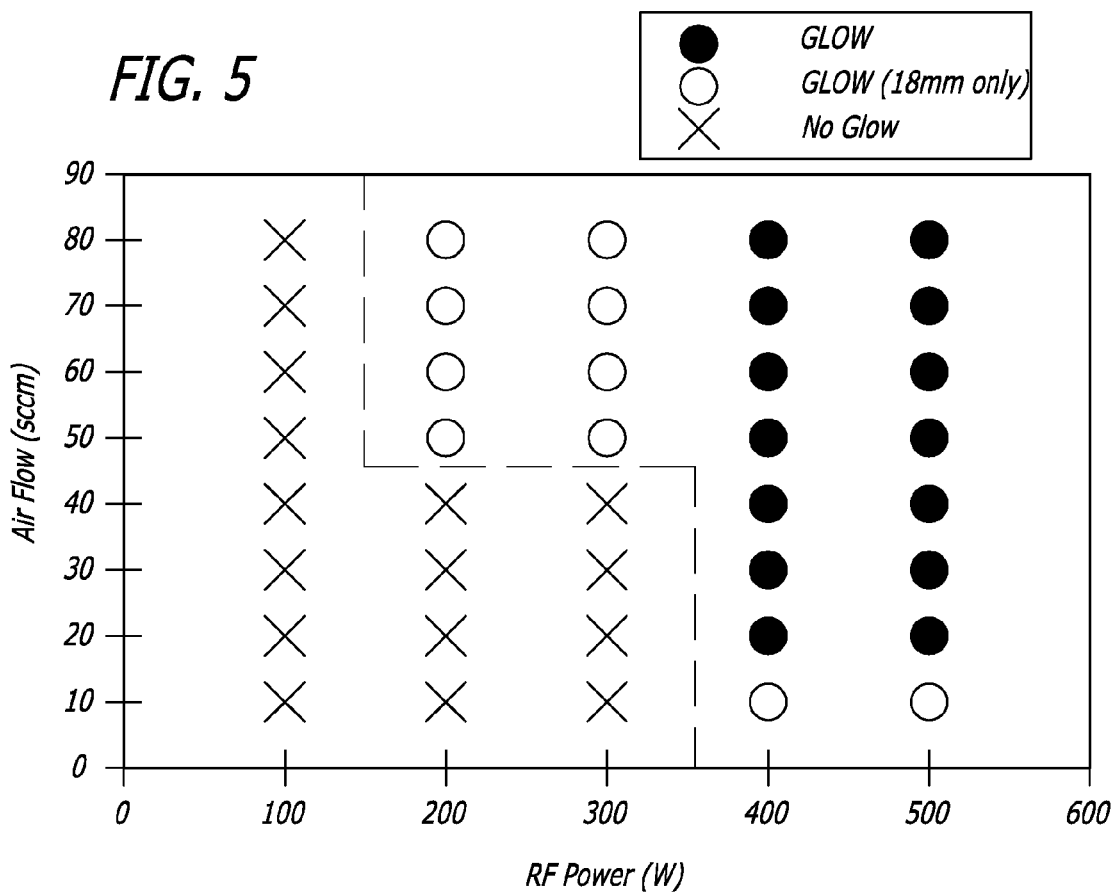
FIG. 5 graphically depicts the conditions for the self-heating of MP35N alloy vascular stents, in the configuration of FIG. 4, where a sample platform/electrode comprises a post on which a stent is placed and a glow at the top of the stent is observed in accordance with the teachings of the present invention.

In still other embodiments of the present invention, surface heating may result in an observable substrate glow as depicted in FIG. 4 at 38. FIG. 5 graphically depicts the correlation between glow and RF power as a function of gas flow. In some embodiments of the present invention, the metallic medical devices generate a secondary plasma (FIG. 4 at 40) which is plasma that is independent of the original plasma source, resulting from the specific orientation of the metallic medical device with regard to the chamber and RF field.

Figure 6:
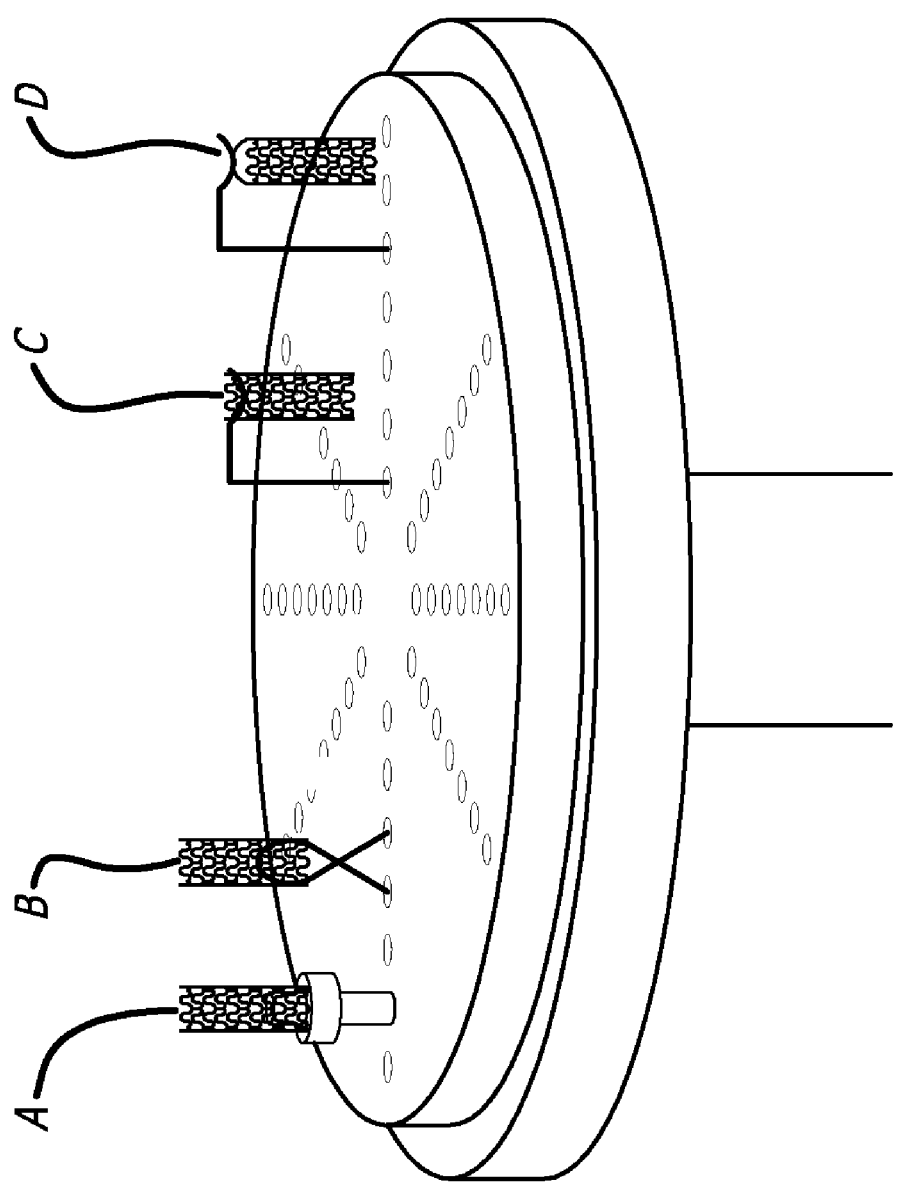
FIG. 6 depicts four configurations of a sample platform/electrode for holding medical device substrates to be textured in accordance with the teachings of the present invention. Holder A comprises a post while Holder B comprises a wire loop. Holders C and D comprise thin wires.

The positioning of the substrate in the plasma chamber results in different textures of the medical devices. FIG. 6 depicts several different substrate holders that are useful for texturing medical devices to provide uniform or non-uniform texturing. Portions of the medical device can be masked from texturing by adjusting the length of inner post of Holder A, for example. Holder A is particularly useful with tubular substrates such as, but not limited to, stents. Altering thermal transport between a substrate and a holder and using a thermal gradient between the two introduces a gradient texture on the substrate. During texturing, thermal energy from a substrate is drawn out through a holder to a platen before the substrate reaches thermal equilibrium. Therefore, a thermal gradient exists. This thermal gradient can be used to produce substrates with gradient textures. In one embodiment, the mass of Holder A can act as thermal sink thereby creating a gradient between the substrate and the holder. The gradient is proportional to mass of the holder, the higher the mass of a substrate holder, the greater the thermal gradient. Therefore, substrates textured on Holders B and C which have less mass than Holder A, thus have less graded and more uniform textures compared to substrates coated on Holder A. Substrates textured on Holder D have a further reduction in thermal gradients by the addition of a thinner wire loop to Holder C and thus limiting the heat sink path. In one embodiment, a wire ribbon is inserted into the inner diameter of a stent (Holder B) and exposed to the texturing process. The area of stent near the tip of the wire ribbon (the middle of a stent in this figure) has minimum texturing compared to the rest of the vascular stent. Thus by adjusting the location of a wire ribbon inside a stent, control is exercised over the parts of the vascular stent being textured.

The RF power supply is also a controlling factor in the generation of non-reactive gas plasma and consequently surface heating and the texturing process. In one embodiment of the present invention, a range of RF power from about 5 watts to about 5,000 watts is provided by the RF power supply, this power range is sufficient to provide a gas phase plasma useful for texturing surfaces. In another embodiment, a range of RF power from about 50 watts to about 2,000 watts is provided by the RF power supply. In yet still another embodiment, a range of RF power from about 75 watts to about 1,000 watts is provided by the RF power supply. In another embodiment, a range of RF power from about 100 watts to about 800 watts is provided by the RF power supply. Alternatively, voltage can also be used as a controlling factor. In one embodiment, a range of voltage from about 50 volts to about 2000 volts is provided by the RF power supply. In another embodiment, a range of voltage from about 400 volts to about 1000 volts is provided by the RF power supply.

The frequency generated from the RF source is an additional controlling factor in the texturing process. In some embodiments of the present invention, the operating frequency, the frequency generated from the RF source, ranges from about 10 KHz to about 80 MHz. This frequency range is sufficient to provide a gas phase plasma and RF field effect useful to achieve surface heating and substrate surface texturing. In additional embodiments, the operating frequency ranges from about 40 KHz to about 28 MHz. In still other embodiments, the operating frequency ranges from about 2 MHz to about 14 MHz. In one embodiment of the present invention, the operating frequency is approximately 13.56 MHz.

Moreover, as briefly discussed above, the medical device exposure period is a factor that influences the texturing process. In one embodiment of the present invention, the texturing time ranges from about 2 seconds to about 600 minutes. In still another embodiment, the texturing time ranges from about 30 seconds to about 15 minutes. In still another embodiment, the texturing time ranges from about 1 minute to about 10 minutes.

Figure 11:
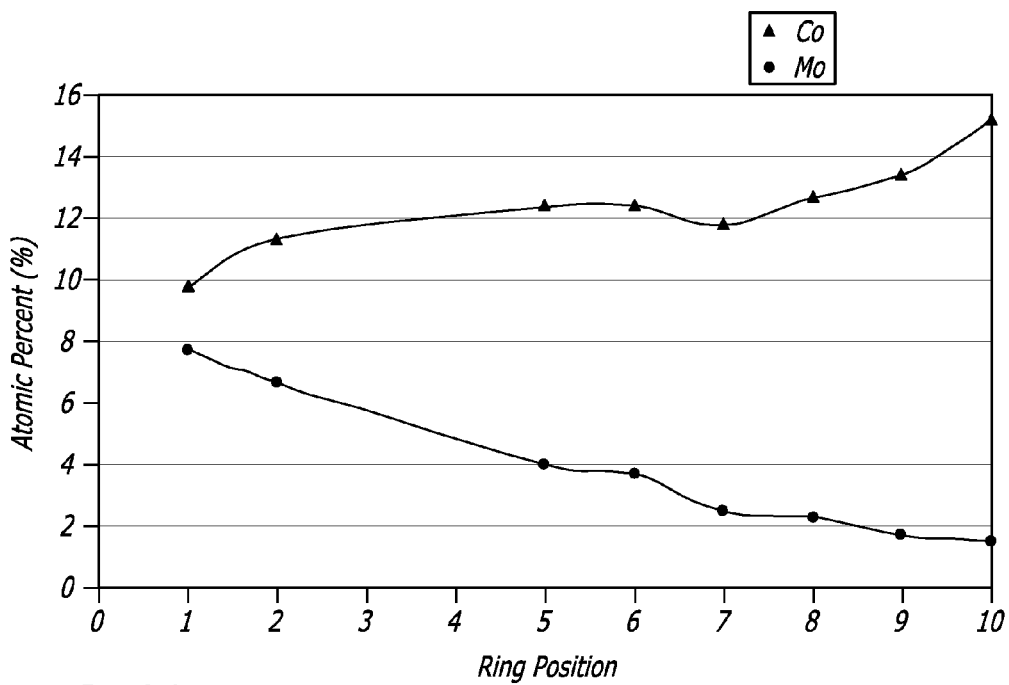
FIG. 11 graphically depicts the disposition of molybdenum and cobalt on a MP35N vascular stent with respect to ring position on the stent in accordance with the teachings of the present invention.
Figure 12:
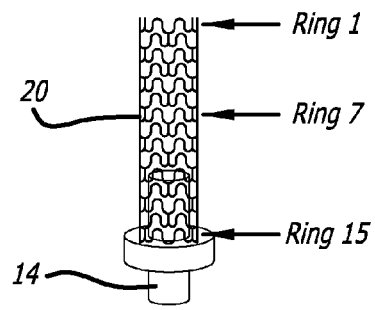
FIG. 12 schematically depicts the elemental composition of MP35N alloy vascular stent ring surfaces made in accordance with the teachings of the present invention.

Elemental analysis of textured substrate surfaces reveals an element disposition gradient with respect to spatial substrate positioning within the process chamber (see FIGS. 11 and 12). In an embodiment of the present invention, a change in elemental composition, as revealed by elemental analysis, is observed through a gradient in the material. In some embodiments of the present invention, a range from about 0.01% to about 99.99% change of specific elements in the material occurs as a result of treatment with plasma. In still another embodiment, a range from about 1% to about 99% change of specific elements in the material occurs as a result of treatment with plasma. In another embodiment, a range from about 5% to about 95% change of specific elements in the material occurs as a result of treatment with plasma. In still another embodiment, a range from about 45% to about 55% change of specific elements in the material occurs as a result of treatment with plasma.

Figure 9:
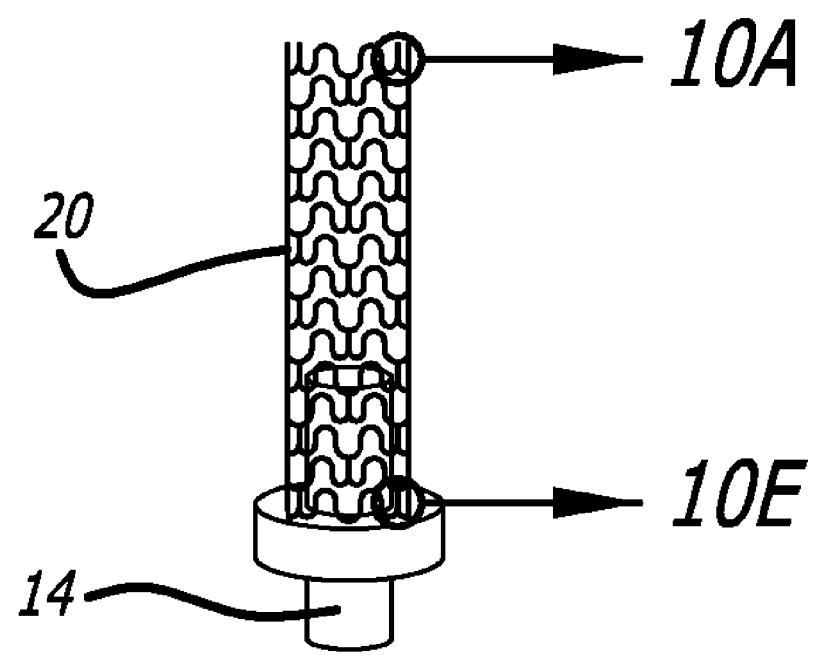
FIG. 9 depicts the post on which a MP35N alloy vascular stent is placed, indicating the top ring (10A) and bottom ring (10E) in accordance with the teachings of the present invention.
Figure 10:
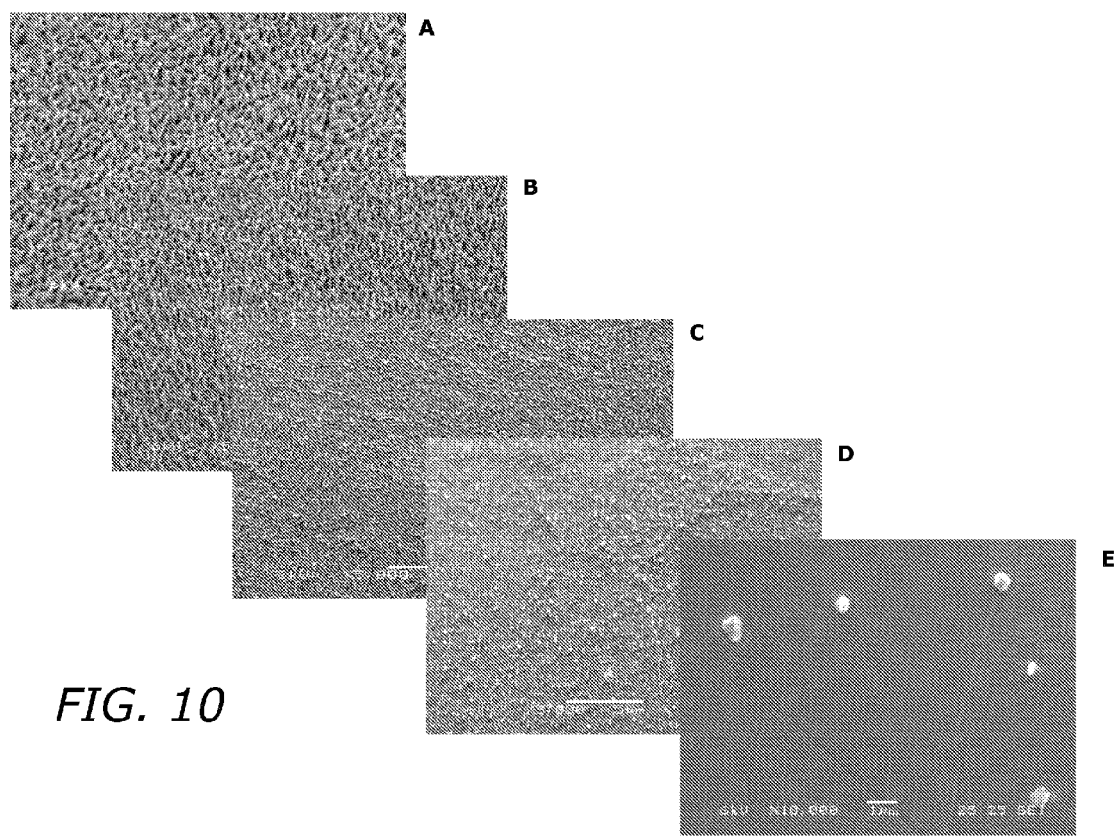
FIG. 10 depicts the textured surface gradient of the MP35N alloy vascular stent depicted in FIG. 9 from the top ring (ring 1, FIG. 10A) to the bottom ring (ring 15, FIG. 10E) in accordance with the teachings of the present invention.

Furthermore, FIGS. 9-10 depict the substrate position effect relative to an attachment fixture 14. As depicted in FIG. 9, in one embodiment of the present invention, the rings of stent 20 have a substantially greater texture at the top (farther from the heat sink 14 see FIG. 10A) than near the bottom (nearer heat sink 14 see FIG. 10E). The textured surface morphology of rings between ring 1 (FIG. 10A) and ring 15 (FIG. 10E) are depicted in FIGS. 10B-D. Moreover, the greater the exposure period, or the more intense the exposure (either as a function of time or proximity to the electrode) the more the elemental composition at the surface varies. For example FIG. 11 graphically depicts the change in cobalt and molybdenum concentrations relative to ring position in a MP35N alloy stent. Ring 1, as depicted in FIG. 12, is farther from the electrode than ring 15, and ring 7 is situated approximately in between rings 1 and 15. As previously observed by reference to FIGS. 9-10, significantly more surface texturing is experienced the farther the stent ring is from the electrode.

Many different materials can be surface textured using the teachings of the present invention. For example, medical devices comprising titanium and its alloys, copper and its alloys, tantalum and its alloys, cobalt-chromium-nickel and their combined alloys, stainless steel, nickel-titanium alloys, aluminum, ceramics, metal matrix ceramic composites, metal coated metals, ceramic coated metals, metal coated polymers, polymer-metal composites and conducting polymers can be surface textured. In one embodiment, the medical device is metallic and is comprised of a metallic material selected from the group consisting of MP35N alloy (a nonmagnetic, nickel-cobalt-chromium-molybdenum alloy), commercially pure titanium (CP-Ti), platinum-iridium (10% wt. Ir) and Ti-6Al-4V (an alpha-beta titanium alloy that includes approximately 6% Al and 4% V depending on the grade).

Figure 7:
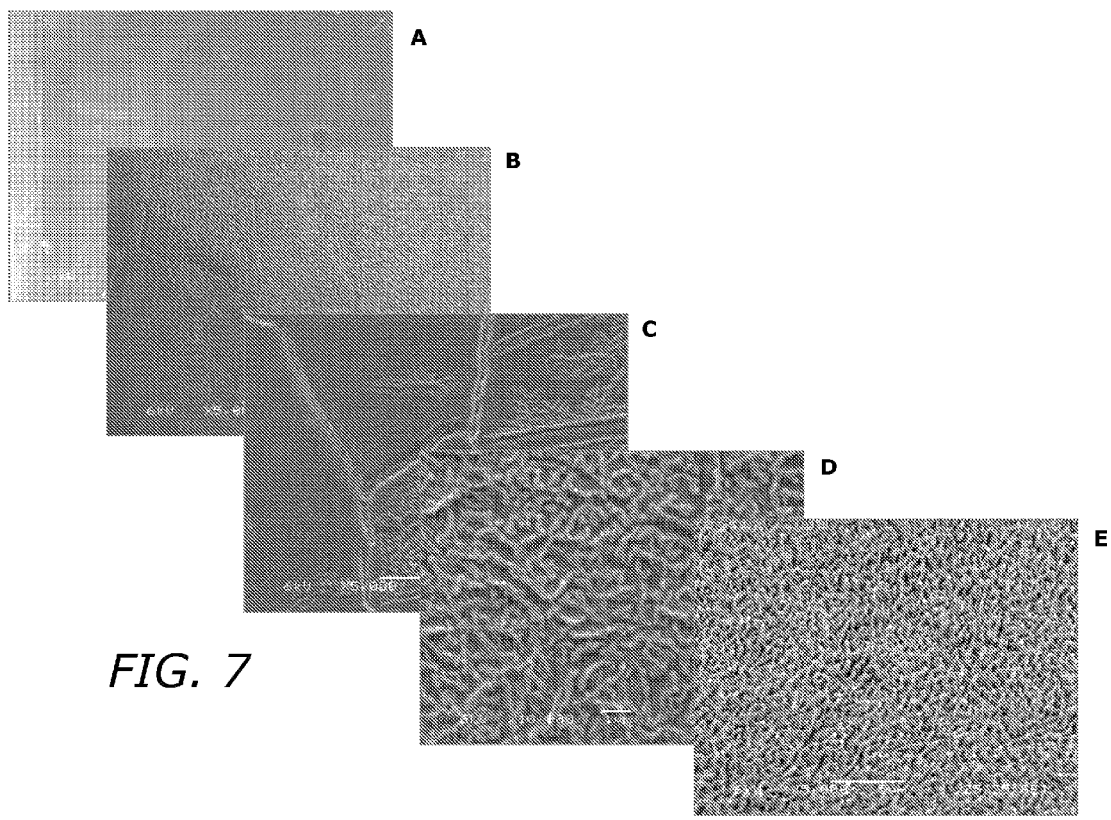
FIGS. 7A-E depict the surface of a MP35N alloy vascular stent over time from five seconds (FIG. 7A) to 600 seconds (FIG. 7E) with respect to the texturing process in accordance with the teachings of the present invention.
Figure 8:
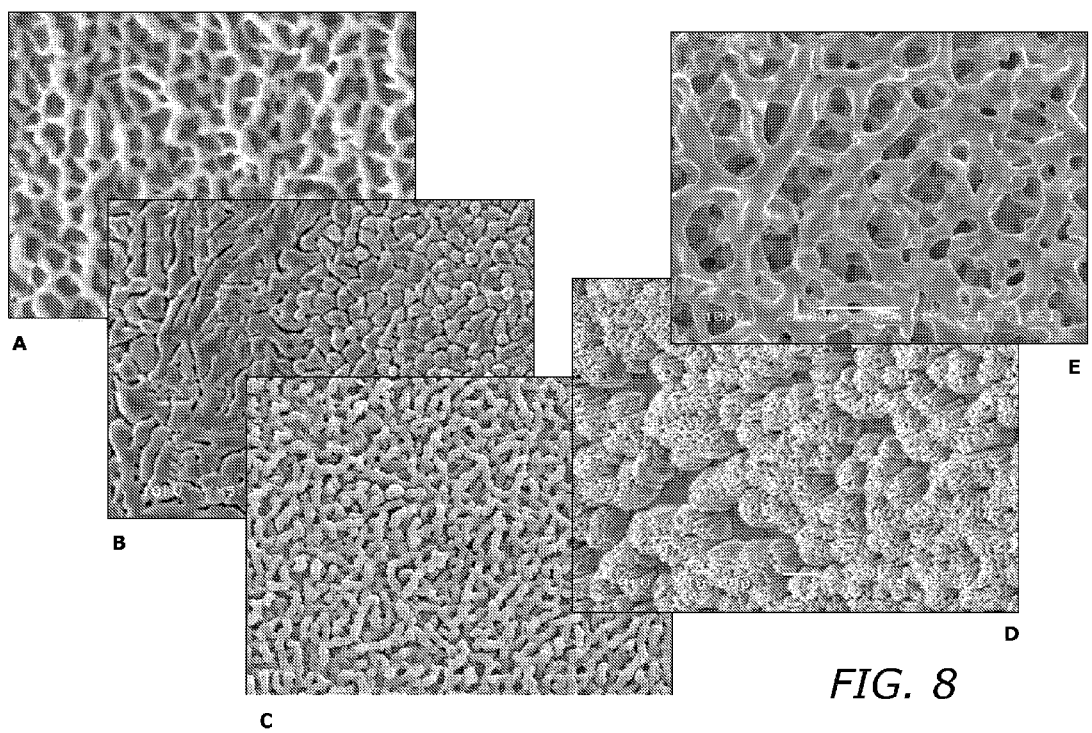
FIGS. 8A-E depict the various textured surface morphologies of metal substrates made in accordance with the teachings of the present invention including morphologies referred to as 'cantaloupe' (on MP35N metal alloy, FIG. 8A), 'brain' (on MP35N metal alloy, FIG. 8B), 'worms' (on MP35N metal alloy, FIG. 8C), 'roses' (on platinum-iridium alloy, FIG. 8D) and a three dimensionally interconnected porous structure (on MP35N metal alloy, FIG. 8E).
Figure 13A:
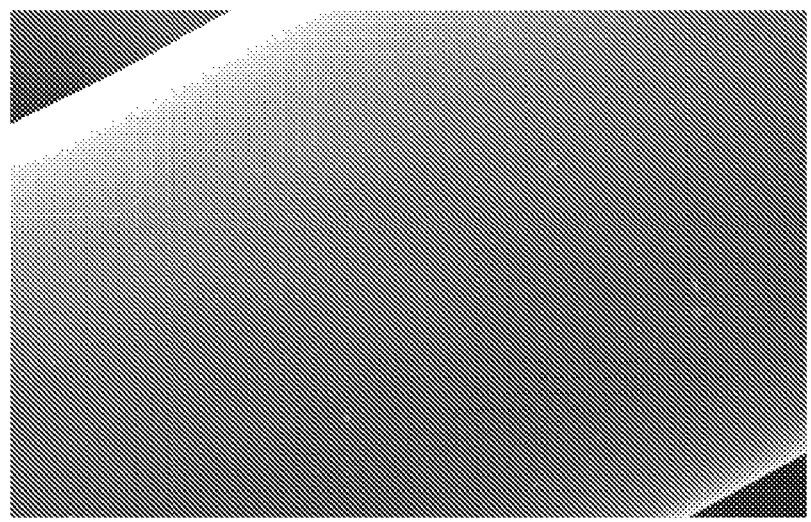
FIGS. 13A-B depict the surface of a textured MP35N alloy stent before (FIG. 13A) and after (FIG. 13B) argon plasma texturing (×1,000) in accordance with the teachings of the present invention.
Figure 13B:
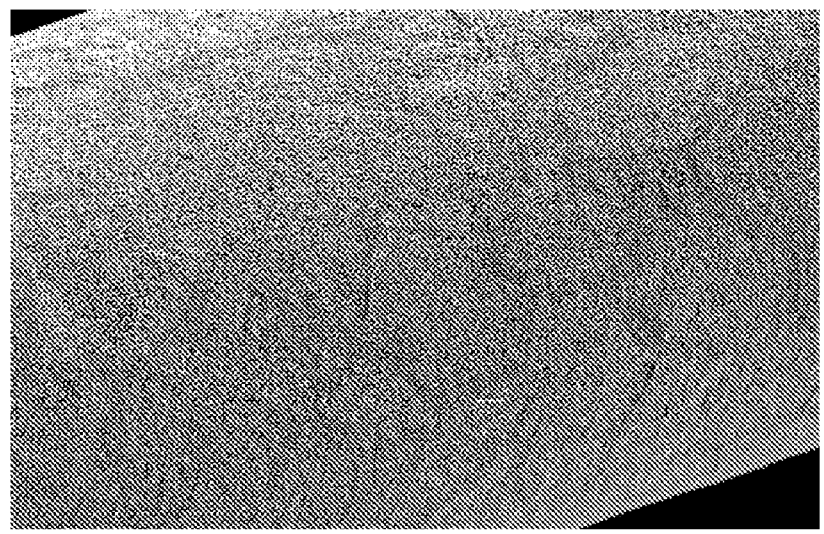
Figure 14:
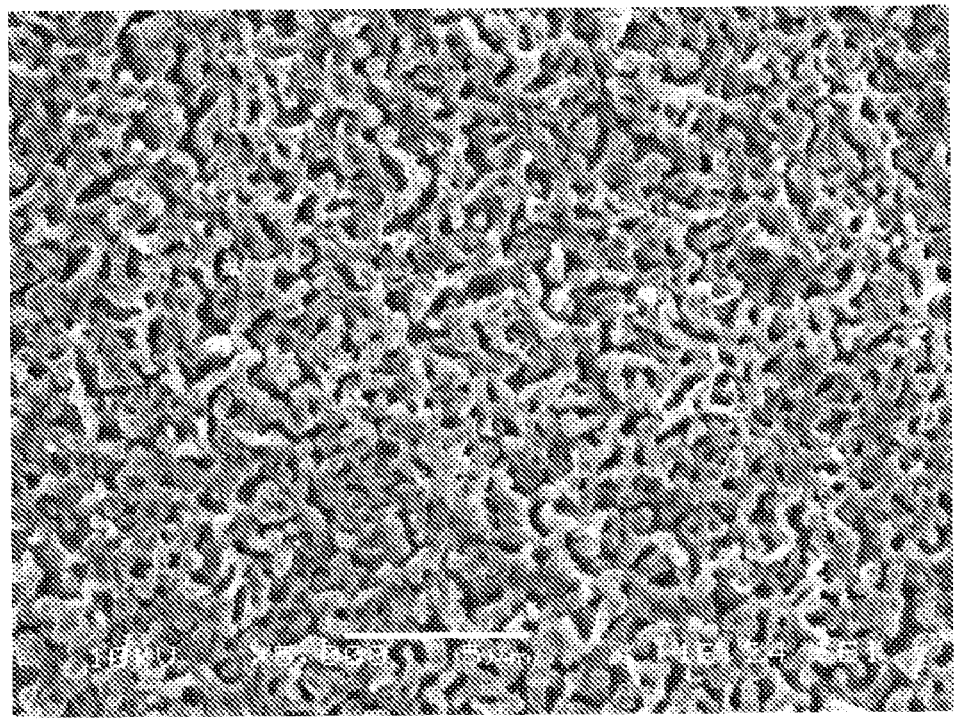
FIG. 14 depicts a textured surface on a commercially pure titanium wire made in accordance with the teachings of the present invention.
Figure 25:
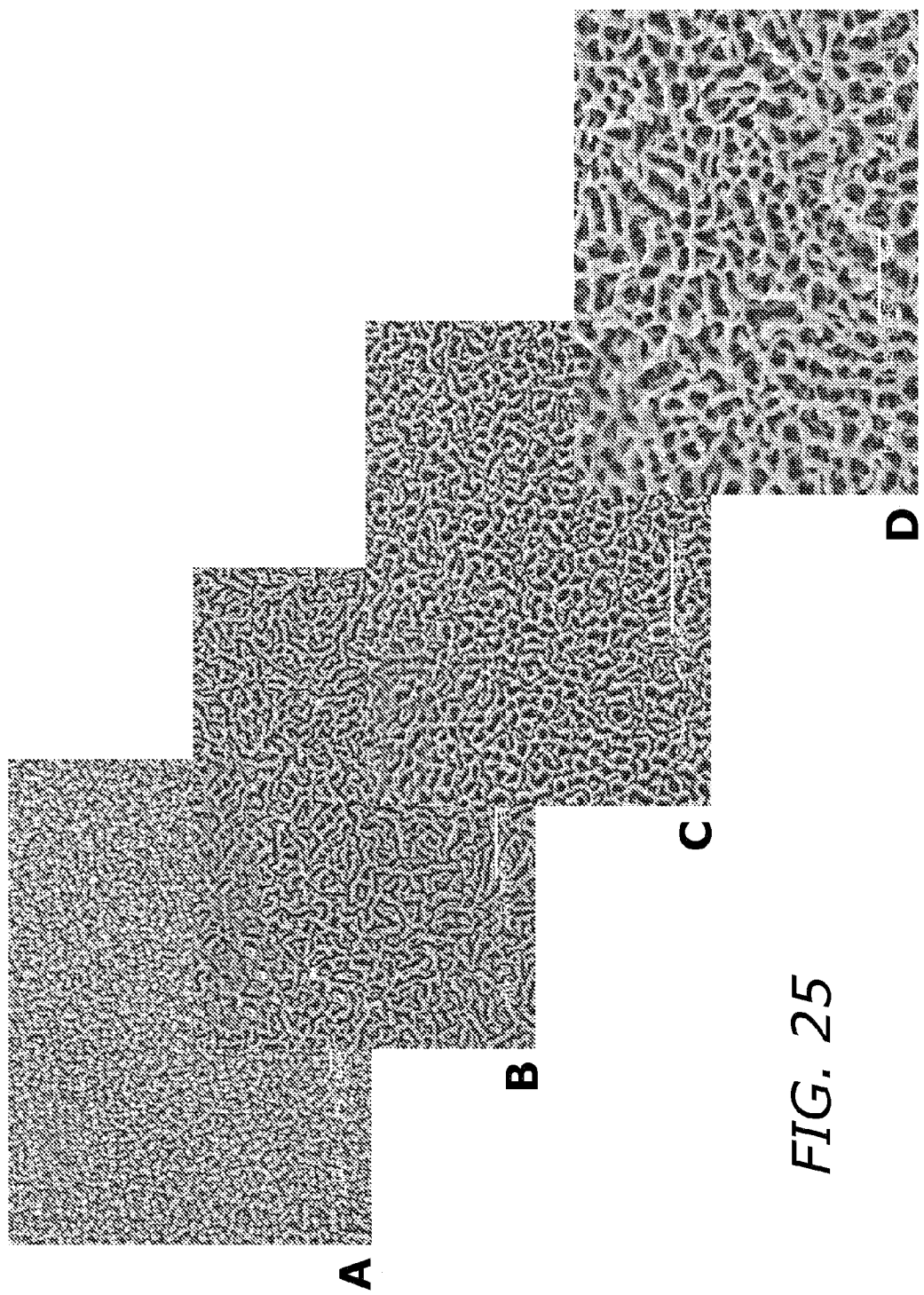
FIG. 25A-D depicts the continuous change in texture morphology from pillar morphology (FIG. 25A) to a brain morphology (FIG. 25B) to a cantaloupe morphology (FIG. 25C) to a three dimensionally porous structure (FIG. 25D) by controlling the temperature of the substrate according to the teachings of the present invention.

The textured surfaces disclosed herein may have distinct morphologies depending on substrate composition, exposure time, process pressure and exposure temperature. FIG. 13A depicts the surface of a metallic medical-grade wire prior to surface texturing and FIG. 13B depicts the same metallic medical-grade wire after being surface textured according to the methods of the present invention. Non-limiting examples of other surface morphologies achievable based on the teaching of the present invention are depicted in FIGS. 7, 8, 10, 13-17, and 25-29. Non-limiting representative texture morphologies are referred to herein as 'cantaloupe' (FIGS. 8A, 25C), 'brain' (FIGS. 8B, 25B), 'worm' (FIGS. 8C, 29), 'pillars' (FIGS. 16, 25A, 26), 'three dimensional interconnecting porous structure' (FIGS. 8E, 25D, 27), 'volcanoes' (FIG. 17) and 'rose' (FIGS. 8D, 25). Generally, the present inventors have surprisingly discovered that surface morphology is a function of exposure time, placement of the medical device relative to the plasma source or electrode, non-reactive gas selection, RF frequency, power output in watts or volts, and process pressure. However, the present inventors have also surprisingly discovered that process time and substrate position relative to an attachment fixture can uniquely affect surface texturing dynamics. The inventors theorize, although not to be bound by this theory, that the proximity to the electrode results in reduced heating as a result of the attachment fixture 14 acting as a heat sink. There is a demonstrable correlation between heating, and the change in texture morphology and elemental composition. This correlation is depicted in FIGS. 9-10 and 13.

For example, short exposure periods (5 seconds) result in relatively minimal surface textures as depicted in FIGS. 7A-E. Further, as exposure times increase the complexity of the textured surface morphology increases. This is illustrated in FIGS. 7C-E wherein the surface of the device in FIG. 7C has experienced a shorter exposure time relative to FIG. 7D and the surface in FIG. 7D was exposed for a shorter time than the surface in FIG. 7E.

Figure 29:
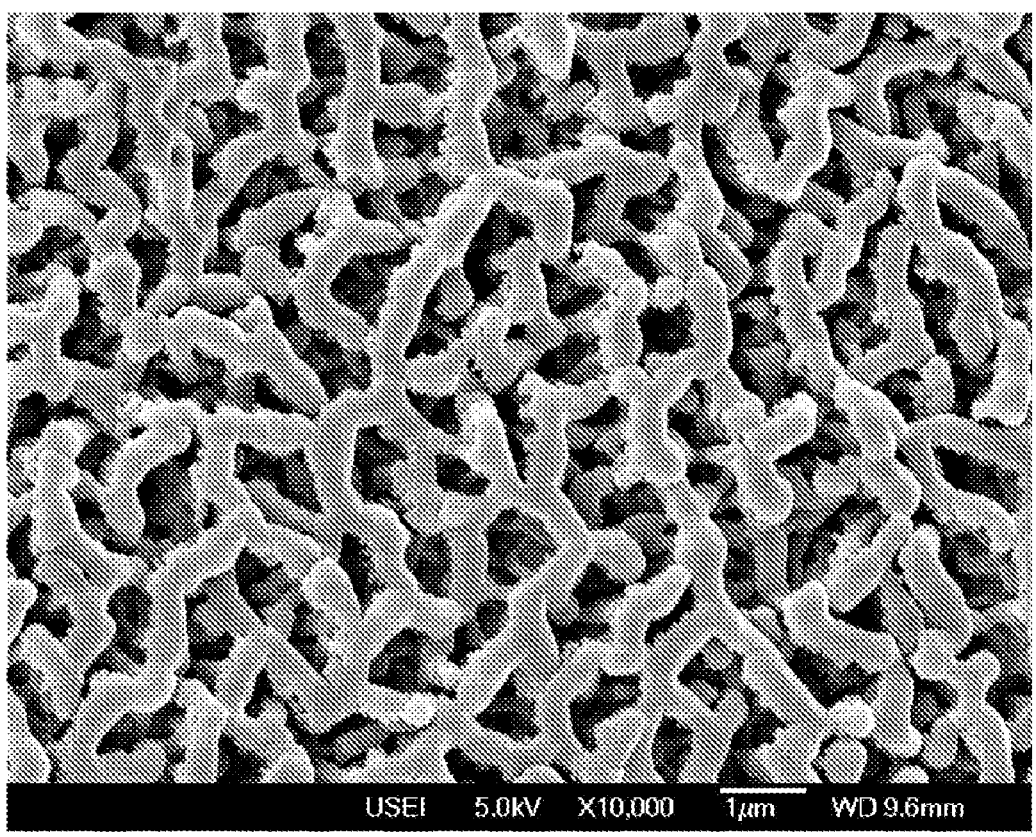
FIG. 29 depicts a 'worm' surface texture morphology formed on a MP35N metal alloy substrate according to the teachings of the present invention.

FIGS. 8C and 29 depict another surface morphology according to the present invention where the surface texture is referred to as 'worm' morphology. In this embodiment, the worm-like structures in FIG. 8C and 29 are formed using a secondary methane deposition after plasma texturing treatment. Thus, the worm morphology structures in FIGS. 8C and 29 comprise a carbon coating rather than the native sample material alone as depicted in FIGS. 7A-E and FIGS. 8A, B, D and E.

Figure 17:
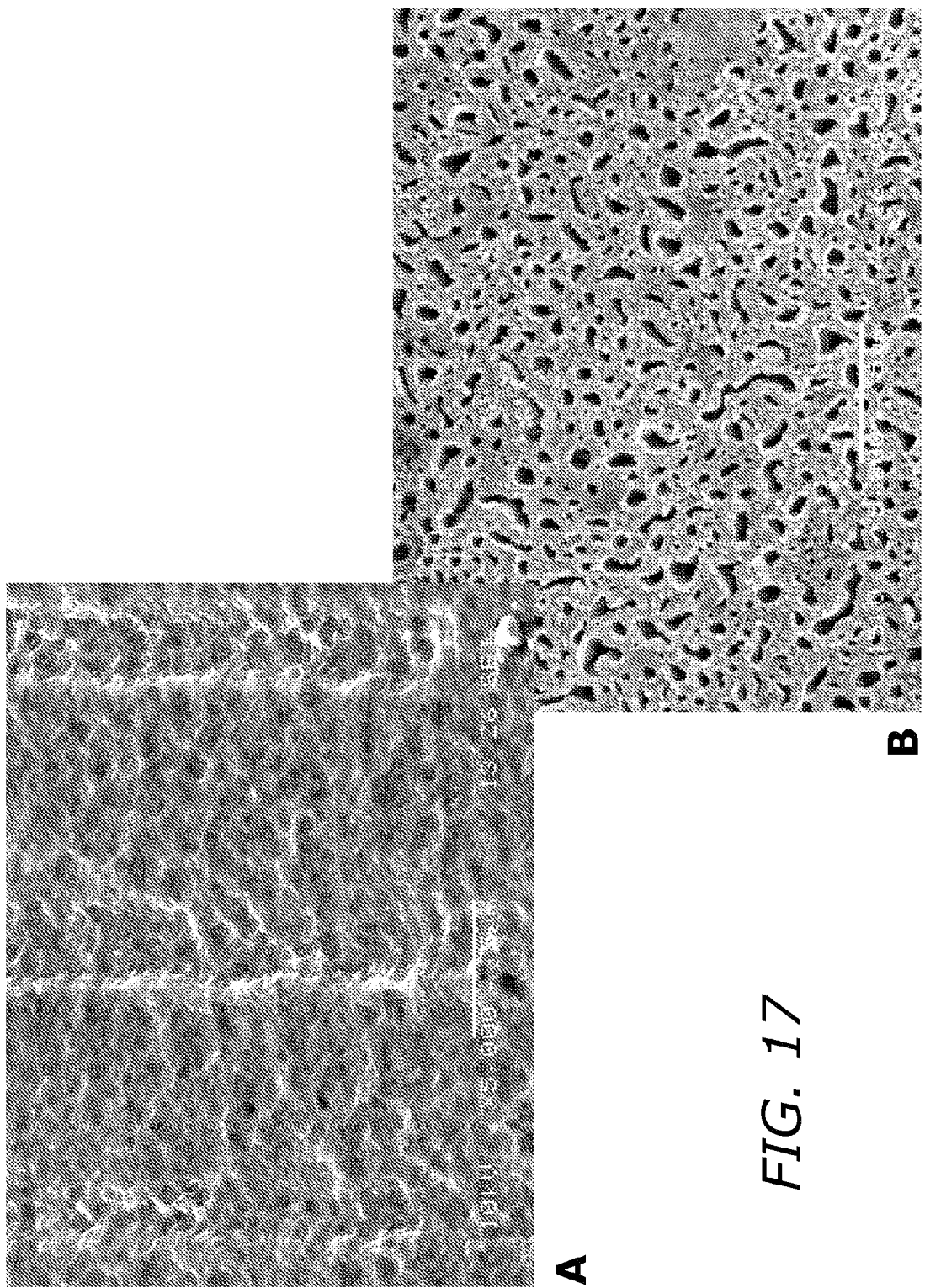
FIG. 17A-D depicts an untextured (FIG. 17A) and textured (FIG. 17B) Ti-6Al-4V alloy dowel having sub-micron sized pores in the surface made in accordance with the teachings of the present invention.
Figure 17:
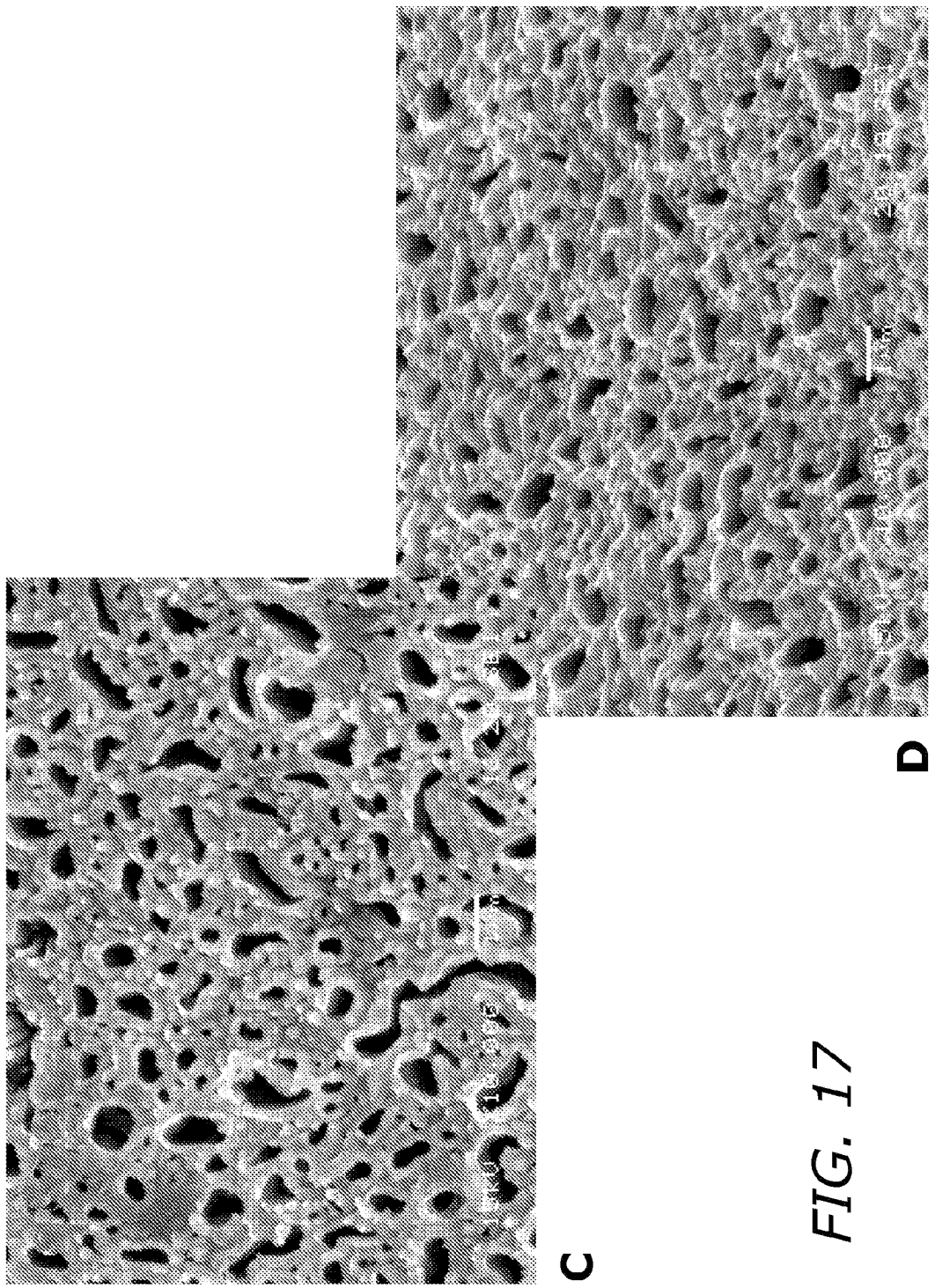

FIGS. 17A-C depicts an additional surface morphology embodiment of the present invention. In FIG. 17, a titanium alloy dowel (Ti-6Al-4V) has been surface textured to form a morphology comprising sub-micron pores or wells termed 'volcanoes' by the present inventors.

Therefore, based on the teachings of the present invention, the surface morphology, and corresponding elemental composition, can be altered using the plasma treating methods of the present invention. Specifically, a medical device surface texture can be incrementally altered from the untreated state (see FIG. 13A) to achieve one or more of the surface morphologies depicted in FIGS. 7, 8, 10, 13-17, and 25-29. The extent of surface texturing can be precisely adjusted by controlling plasma temperature, device surface temperate and exposure time. Those parameters are controlled by RF frequency, power output in watts or volts, chamber pressure and non-reactive gas flow. Additionally, surface heating can be controlled using heat sinks and placement location within the chamber relative to the RF electrodes.

The texturing methods presented herein also include the combined system of inductively coupled plasma and induction heating. Induction heating heats the medical device substrate instantly by placing an induction coil around it and applying power through the coil. The power supply sends alternating current through the coil, generating a magnetic field. When the substrate is placed in the coil, the magnetic field induces eddy currents in the substrate, generating localized heat without any physical contact between the coil and the medical device substrate. The effective frequency range used for induction heating is between 1 kHz and 60 MHz, depending on the size of the substrate. There is a relationship between the frequency of the alternating current and the depth to which it penetrates in the medical device substrate; low frequencies of 5 to 30 kHz are effective for thicker materials requiring deep heat penetration, while higher frequencies of 100 to 400 kHz are effective for smaller parts or shallow penetration. For heating very small parts, frequencies up to 60 MHz may be used. Furthermore, the RF plasma system operates commonly at 13.56 MHz, which falls in the frequency range that can generate induction heating. Therefore, induction heating and plasma generation are coupled into one system to offer a combined plasma/induction heating to texture the medical device substrate by both heating and by plasma generation simultaneously.

Additionally, coupling of the two systems may require having two separate RF power supplies depending on the optimum frequency to inductively heat the medical device and to generate plasma. To that effect a frequency blocker or any circuitry that prohibits interference between two different frequencies can be included.

The methods of the present invention also produce substrate self-heating from RF plasma conditions. Therefore, substrates with inorganic coatings can be formed to produce high temperature inorganic materials without an external heat source. Certain inorganic compounds are stably formed generally at elevated temperatures, such as diamond, graphite, carbon nanotube, silicon dioxide, titanium oxide, or any metal oxides, carbides, or nitrides. To obtain such compounds on a substrate under a normal plasma-enhanced chemical vapor deposition (PE-CVD) conditions, gaseous precursors are introduced into a chamber while the substrate is heated to temperatures above 500° C. However, if a metal substrate is placed under the RF plasma conditions in accordance with the teachings of the present invention, the metal substrate will be self-heated to sufficiently high temperatures such that inorganic compounds can be stably formed on the substrate without applying heat from an external source. In one embodiment, carbon films are deposited on a vascular stent (FIGS. 8C and 29).

The textured medical device surfaces created by the plasma texturing technique described herein additionally provides useful adhesion properties. The modified surfaces can improve the adhesion of coatings applied from solutions in Example 11). In one embodiment of the present invention the adhesion of biocompatible polymers to textured vascular stents is enhanced. In another embodiment the adhesion of biodegradable polymers to textured vascular stents is enhanced.

Furthermore, the morphology and surface area of textured medical devices sufficiently increases the ability of the surface to act as drug (bioactive agent) reservoirs. The term "reservoir" refers to a space such as, but not limited to a cavity or a pore, that can hold bioactive agents on the surface of a substrate including, in one example, an implantable medical device. The textured medical device can further comprise a coating which can function as a drug reservoir by releasing one or more bioactive agents from the coating.

Examples of bioactive agents useful for elution from medical devices include, but are not limited to, steroids, drugs for reducing restenosis after stent implantation (for example rapamycin), proteins and other biologics, such as bone morphogenic protein (BMP), drugs to reduce pain and promote healing, and bioactive coatings. Additional bioactive agents are listed in the Definition of Terms section. In one embodiment, steroid eluting lead tips are produced. In another embodiment, steroids, including, but not limited to, dexamethazone and belcomethasone are added to the textured defibrillation coil of a bipolar tachycardia lead to reduce thrombus and fibrous capsule formation and improve the ability of the lead to be removed. In another embodiment, the release of the bioactive agent from the reservoir is controlled with a biodegradable cap coat such that upon the degradation of the cap coats, the bioactive agent is released.

In one embodiment of the present invention, post-texturing treatments of the textured medical devices are provided. Exposing the textured, heated metal substrate to different reactive atmospheres with or without a source of energy provides an adhesive surface suitable for further coating. One exemplary reactive atmosphere, a carbon rich atmosphere, comprises methane, ethane, propane and other carbon-based gases and solutions.

A similar approach is taken to modify the surface of the textured medical device to render the surface either hydrophilic or hydrophobic. In one embodiment, the heated textured medical device surface is exposed to oxygen and water to form a hydrophilic surface. Alternatively, in another embodiment, the heated textured surface is made hydrophobic by exposure to a fluorine-containing atmosphere such as, but not limited to, tetraflouroethylene.

Additionally, post-texturing treatment of medical devices provides improved biocompatibility by exposing the textured substrate to a carbon rich atmosphere energized by an additional energy source such as a plasma or ion beam resulting in the deposition of a diamond, amorphous carbon or diamond-like carbon coating. This coating forms additional surface features resulting in a finer textured coating on the initial nanometer to micrometer scale textured surface. The added surface area provides additional opportunities for chemical bonding and the surface features can mechanically interlock with the deposited coating.

Furthermore, post-texturing treatments of selected medical devices enhances other surface properties. Modifying the chemistry of the textured surface can improve the wetting, coating uniformity and adhesion of coatings subsequently applied from solutions. The textured surfaces provide points of adhesion for polymers, including but not limited to, biocompatible polymers, biodegradable polymers, carbon-based polymers, and silicon-based polymers. In one embodiment of the present invention, an oxygen-treated medical device has a hydrophilic surface that improves the adhesion of a hydrogel coating. In another embodiment, the oxygen-treated medical device is coated with polysaccharides. Exemplary polysaccharides include, but are not limited to, hyaluronic acid, glucosamine, chitosan, and dextran. In another embodiment, proteins are used to coat the oxygen-treated medical device. In another embodiment, collagen is used to coat the oxygen-treated medical device. In yet another embodiment, antimicrobial coatings such as but not limited to poly methylaminomethylstyrene, furanone, silver, quaternary ammonium compounds, are also used to coat oxygen-treated medical device. In another embodiment, anti-thrombogenic coatings comprising heparin are also used to coat an oxygen-treated medical device.

The texturing of medical devices such as, but not limited to, vascular stents, also provides for surface and structural integrity. For example, upon expansion of vascular stents, textured with the methods of the present invention, cracking of the surface in the vicinity of the joints is reduced. Upon expansion of polymer-coated vascular stents, delamination of the coating is observed in non-textured stents. In contrast, textured vascular stents that have been polymer-coated do not delaminate upon expansion (see Example 11). Polymer useful for coating textured medical devices include, but are not limited to, biocompatible polymers, controlled release polymers, biodegradable polymers, acrylate polymers, polyesters, polyorthoesters, polyanhydrides, and the like. Additional examples of suitable polymers are disclosed in co-pending U.S. Patent Application Publication No. 2005/

0084515 A1, which is incorporated herein in its entirety for all it contains regarding biocompatible controlled-release coating for medical devices.

In one embodiment, textured and non-textured stents were coated with polymers containing bioactive agents. The polymer coating on the textured stent did not delaminate and had improved durability compared to non-textured stents.

The polymeric coatings of the present invention are applied in a variety of methods including, but not limited to, spraying and dipping. In one embodiment the textured medical devices are dipped in a solution comprising dissolved polymers and removed to be dried. In another embodiment the textured medical device is sprayed with the dissolved polymer and allowed to dry.

Functionalizing surfaces of the textured medical devices with amine groups provides additional useful surface properties. In functionalizing the textured surface with amine groups, the textured heated medical device is exposed to a mixture of ammonia and a carbon rich atmosphere with or without an additional energy source. This amine rich surface could then be used to bond polysaccharides such as heparin, providing surfaces with anti-thrombogenic properties. In one embodiment, a heated mechanical heart valve ring is treated with ammonia and methane and the surface is then further coated with heparin.

In another embodiment of the present invention, functionalized bone morphogenic protein (BMP), known to promote osteointegration, is added to textured surfaces of implantable orthopedic devices including, but not limited to, bones screws, pins and orthopedic joints that had been exposed to an oxygen-containing environment producing a negative charge on the textured surface. BMP-coated orthopedic implantable medical devices promote bone in-growth and integration. In another embodiment, dental implants are coated with BMP. In one embodiment, screw-shaped dental implants textured by the plasma process are produced and can promote bone in-growth and integration when implanted in the jaw. In another embodiment, artificial temporomandibular joint replacements are textured and coated with BMP to promote osteointegration to the jaw bone.

In one embodiment, the outer surface of a stent or stent graft is textured according to the methods of the present invention to promote cell in-growth (endothelialization) which aides in maintenance of the stent graft in position to prevent endoleak and migration. In yet another embodiment, coatings containing anti-inflammatory drugs such as, but not limited to, dexamethasone and beclomethasone are provided on textured stents and stent grafts to promote healing.

Textured wires can be used as guidewires to position implantable medical devices. In another embodiment, the guidewires are textured according to the methods of the present invention and the textured surface is able to help retain coatings added to the guidewire. In one embodiment, the textured guidewires are coated with a lubricious coating such as, but not limited to, hyaluronic acid or silicone.

In another embodiment, surface texturing according to the present invention is useful for selective texturing of surfaces for promoting the direction growth of nerves or other tissues.

In other embodiments of the present invention, the surface texturing methods disclosed herein are useful for texturing surfaces other than those associated with medical devices. In one embodiment, the surface texturing methods are useful for texturing capacitors to provide a high surface area for high efficiency. In another embodiment, surface texturing according to the present invention is useful for forming mold surfaces for texturing polymers by imprinting the polymer surface. In another embodiment, selective regions are textured for articulating applications by selective masking.

In another embodiment, surface texturing according to the present invention is useful for texturing fibers for manufacture of fiber-reinforced composites. In this embodiment, the texturing increases the interfacial area to increase toughness and strength. In another embodiment, surface texturing according to the present invention creates superhydrophobic surfaces (lotus leaf effect) with the pillar-like texture morphology.

EXAMPLES

The following non-limiting examples serve to illustrate specific non-limiting embodiments of the present invention and are proved to demonstrate the present invention's versatility.

Example 1

Surface Texturing of Metal Wires

Figure 15:
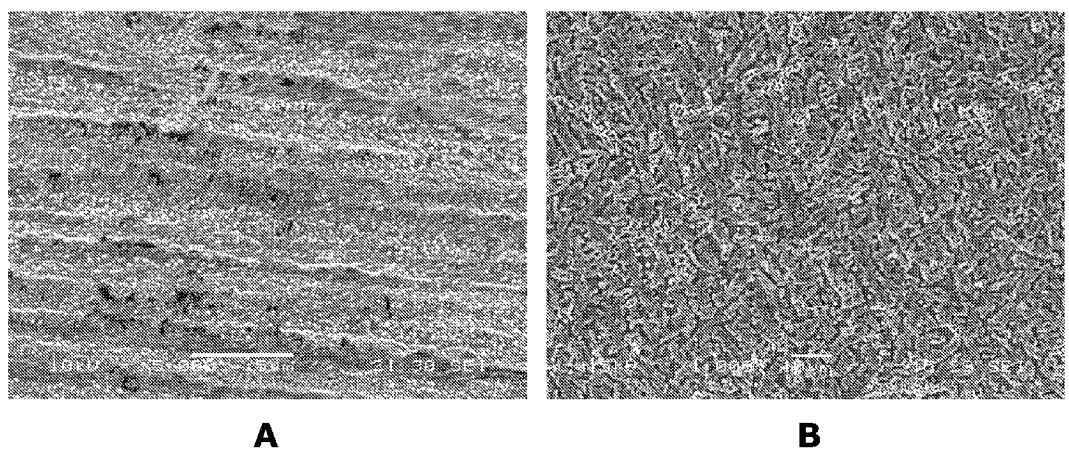
FIG. 15A-B depict a textured surface on a tantalum wire at close to an electrode (more heat sinks, ×5,000, FIG. 15A) and further from an electrode (×1,000, FIG. 15B) made in accordance with the teachings of the present invention.
Figure 16:
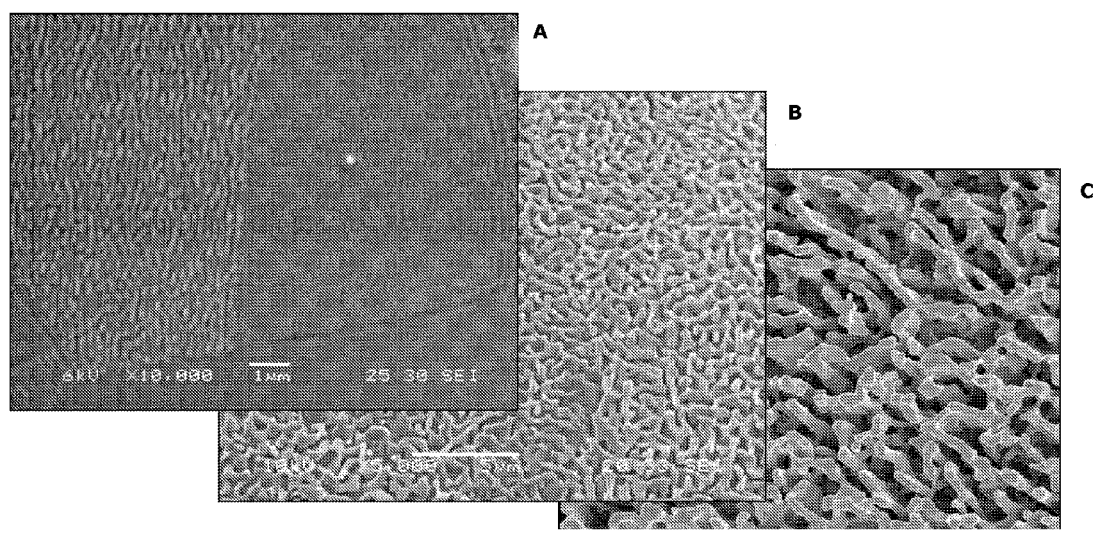
FIGS. 16A-C depicts a pillar surface morphology of a textured MP35N alloy vascular stent formed over time from less than 2 minutes (FIG. 16A) to 10 minutes (FIG. 16C, ×10,000) made in accordance with the teachings of the present invention.

Metal wires (5 cm length, 300 µm diameter) were placed on vertical stainless steel rods and fastened to suspend the wire horizontally. The stainless steel chamber was sealed and a vacuum applied to decrease the atmospheric pressure to about $10^{-6}$ Torr. A flow of argon gas, 30 Standard Cubic Centimeters per Minute (sccm), was then applied from the inlet nozzle resulting in a process pressure of about 41 mtorr. Power (500 watts) from the RF power supply was activated and an argon plasma and RF field effect were generated. The metallic medical devices surface was heated to about 1000° C., without the application of an additional external heat source (the additional heating means in this example is provided by RF field effect), and texturing of metal wires continued for 10 minutes. After 10 minutes had elapsed, the flow of argon gas was ceased and the RF power supply shut down. The metal wires were allowed to cool to ambient temperature before removal from the stainless steel chamber. Using these methods, Group 1 morphology was obtained on commercially pure titanium wire (FIG. 14) and tantalum wire (FIG. 15). FIG. 15 depicts tantalum wire textured closer to the electrode (more heat sinks, FIG. 15A) or farther from the electrode (FIG. 15B).

Example 2

Surface Texturing of Electrodes

Metal leads (platinum-iridium nail shaped electrode, 5 mm length, 500 µm diameter) were screwed in a vertical stainless steel rod. The stainless steel chamber was sealed and a vacuum applied to decrease the atmospheric pressure to about $10^{-6}$ Torr. A flow of argon gas (50 sccm) was then applied from the inlet nozzle resulting in a process pressure of about 67 mTorr. Power (500 watts) for the RF power supply was activated and argon plasma and RF field effect are generated. The metal leads were exposed to the argon plasma for 10 minutes as texturing of metal electrodes by the argon plasma continued. After 10 minutes had elapsed, the flow of argon gas was ceased and the RF power supply shut down. The metal electrodes were allowed to cool to ambient temperature before removal from the stainless steel chamber. As depicted in FIG. 8D, a Group 2 (rose) morphology was obtained on the surface of the Pt—Ir electrode.

Example 3

Surface Texturing of Metal Alloy Dowel

A Ti-6Al-4V metal alloy tubular dowel (13 mm length, 3 mm diameter) was suspended with a MP35N wire (250 μm diameter) from about one third of the length of the dowel. The wires were then placed on the vertical stainless steel rods and fastened. The stainless steel chamber was sealed and a vacuum applied to decrease the atmospheric pressure to about $10^{-6}$ Torr. A flow of argon gas (50 sccm) was then applied from the inlet nozzle resulting in a process pressure of about 67 mtorr. Power (500 watts) for the RF power supply was activated and argon plasma and RF field effect are generated. The Ti-6Al-4V tubular dowel was exposed to the argon plasma for 10 minutes. After 10 minutes had elapsed, the flow of argon gas was increased from 50 sccm to 70 sccm, resulting in a process pressure of about 91 mtorr. The Ti-6Al-4V tubular dowel was then exposed to the argon plasma for 20 minutes. After time had elapsed, the flow of argon gas was ceased and the RF power supply shut down. The Ti-6Al-4V tubular dowel was allowed to cool to ambient temperature before removal from the stainless steel chamber.

FIG. 17A-D depicts an untextured (FIG. 17A) and textured (FIG. 17B) Ti-6Al-4V dowel having sub-micron sized pores in the surface representative of the volcano morphology of Group 3. FIG. 17C is a higher magnification (×10,000) of FIG. 17B (×5,000). FIG. 17D is a tilted angle view of the texture morphology of FIG. 17C.

Example 4

Surface Texturing of Vascular Stents

Vascular stents (MP35N, 18 mm long, 3.5 mm diameter) were textured by placing the stents on stainless steel posts within a chamber. The stainless steel posts are secured to the platform by placing the post on a stainless steel post-holder. The post-holder is in a hole present on the platform. The stainless steel chamber is then sealed and a vacuum applied to decrease the atmospheric pressure to about $10^{-6}$ Torr. A flow of argon gas from about 30 sccm to about 50 sccm is then applied from the inlet nozzle resulting in a process pressure from about 38 mTorr to about 67 mTorr. Power from about 100 watts to about 800 watts from the RF power supply is activated and argon plasma and RF field effect are generated. The stents are exposed to the argon plasma, where the top of the stents increase in temperature to about 1000° C. without the application of an external heat source, for about 5 to about 15 minutes as texturing of stents proceeds. After 10 minutes had elapsed, the flow of argon gas is ceased and the RF power supply shut down. The stents were allowed to cool to ambient temperature before removal from the stainless steel chamber.

FIG. 13 depicts the surface of a textured MP35N alloy stent before (FIG. 13A) and after (FIG. 13B) argon plasma texturing (×1,000). As the texturing time increases, the complexity of the surface morphology increases (FIG. 7). FIG. 7 depict the surface of a MP35N alloy vascular stent over time from five seconds (FIG. 7A) to 10 minutes (FIG. 7E) FIGS. 7B-D depict the surface morphology at time points between 5 seconds and 10 minutes. FIGS. 17A-C depicts additional images of the formation of the pillar surface morphology over time from less than 2 minutes (FIG. 16A) to 10 minutes (FIG. 16C, ×10,000). Furthermore, FIG. 8 depicts texturing of MP35N stents to yield cantaloupe (FIG. 8A), brain (FIG. 8B) and three dimensional interconnecting porous structure (FIG. 8E) surface morphologies.

The texturing is also affected by the distance from the attachment feature, or electrode, in the process chamber. FIG. 9 depicts the post on which a MP35N alloy vascular stent was placed, indicating the top ring (10A) and bottom ring (10E). The texturing of exemplary rings is depicted in FIG. 10. FIG. 10A is the top ring (ring 1) and FIG. 10E is the bottom ring (ring 15). FIGS. 10B-10D depict rings between ring 1 and ring 15.

Example 5

Formation of Group 4 Texture Morphology

In this example, a texture morphology of Group 4 was formed in which a secondary deposition of a carbon coating with a methane gas.

Vascular stents were textured by placing the stents on a fixture within a chamber. The fixture was secured to the platform by placing it in a hole present on the platform. The stainless steel chamber was then sealed and a vacuum applied to decrease the atmospheric pressure to about $10^{-6}$ torr. A flow of argon gas about 30 sccm was then applied from the inlet nozzle resulting in a process pressure about 48 mTorr. Power (500 watts) from the RF power supply was activated and argon plasma and RF field effect were generated. The stents were exposed to the argon plasma for 10 minutes as texturing of stents by the argon plasma continued. After 10 minutes had elapsed, the flow of argon gas was ceased and the RF power supply shut down. The source of gas was then switched from argon to methane, and a flow of methane gas about 10 sccm was applied resulting in a process pressure about 10 mtorr. Power (150 watts) from the RF power supply was activated and methane deposition started. The stents was exposed to the methane plasma for about 5 to about 15 minutes as deposition of methane proceeded. After time had elapsed, the flow of methane gas was ceased and the RF power supply shut down. The stents were allowed to cool to ambient temperature before removal from the chamber.

FIG. 8C and FIG. 29 depict the surface morphology formed by secondary exposure to methane plasma with the formation of a 'worm' surface morphology.

Example 6

Effect of Substrate Temperature on Texture Morphology

Texture morphology changes from pillar structure (FIG. 26A-B) to three dimensionally porous structure (FIG. 27A-C) by controlling the temperature of the substrate.

Figure 26:
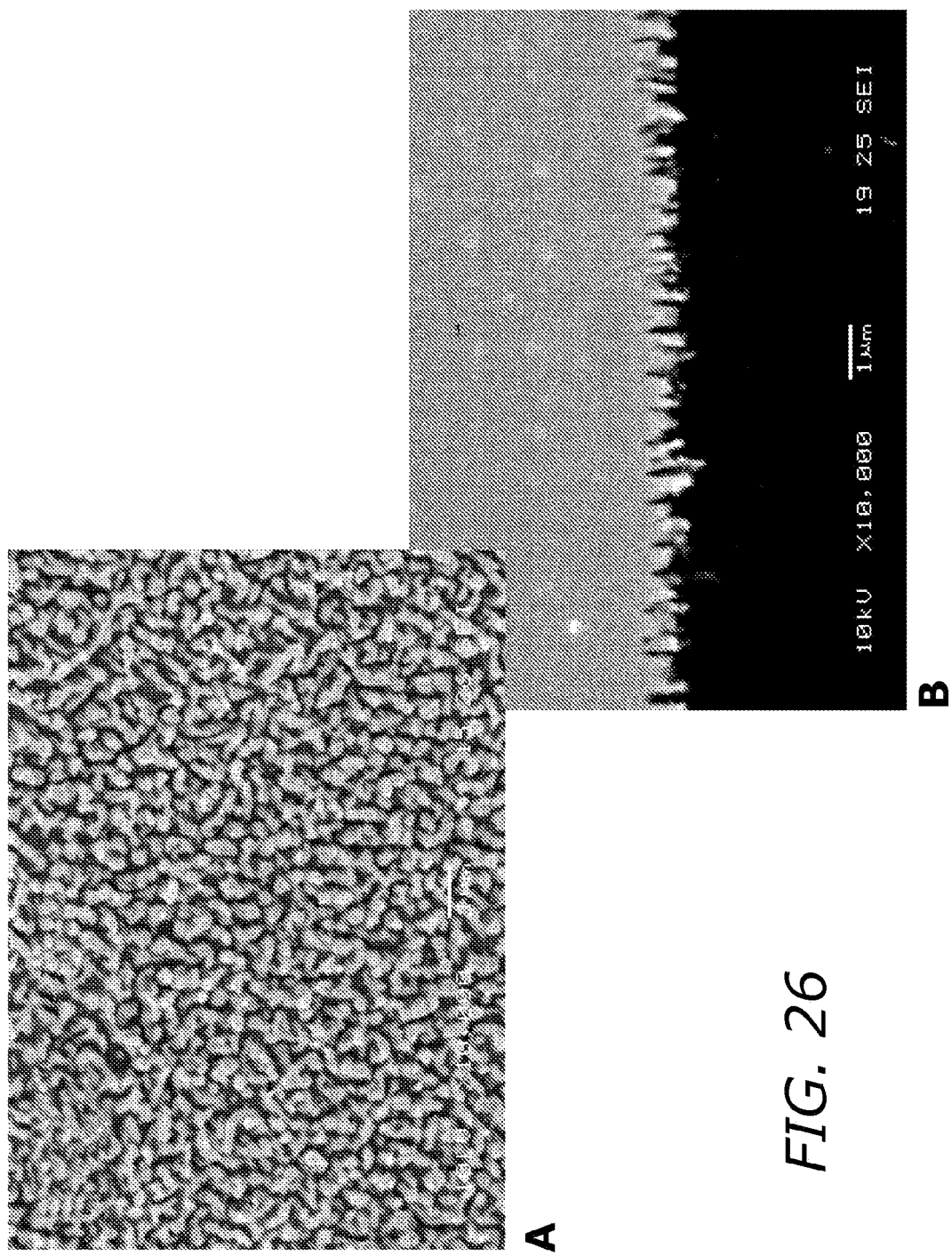
FIG. 26A-B depicts a pillar texture morphology at a top view (FIG. 26A) and a cross-section view (FIG. 26B) according to the teachings of the present invention.
Figure 27:
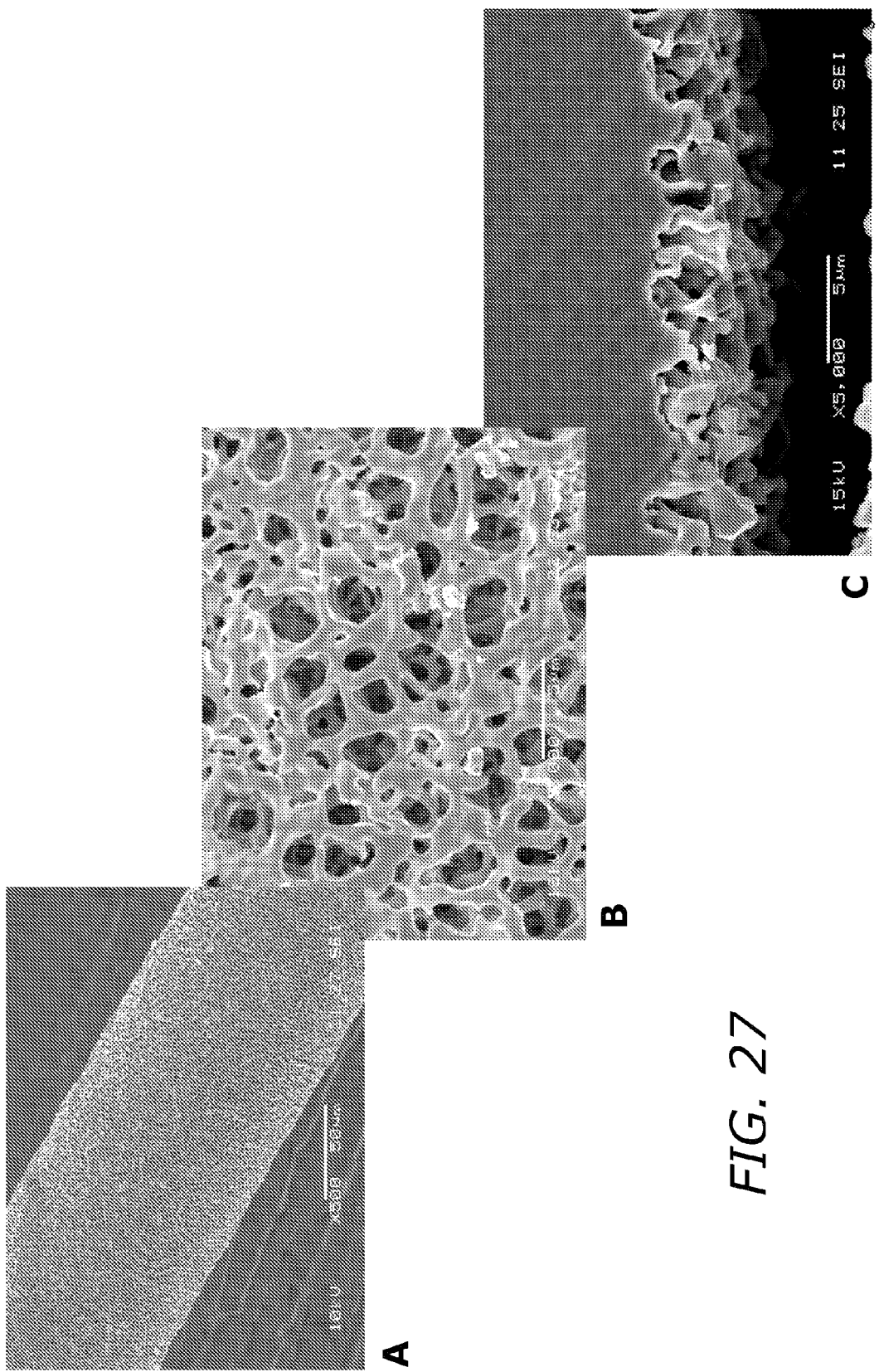
FIG. 27A-C depicts a three-dimensionally interconnected porous structure at low magnification (×500, FIG. 27A), high magnification top view (×5,000, FIG. 27B) and cross-section view (×5,000, FIG. 27C) according to the present invention.
Figure 28:
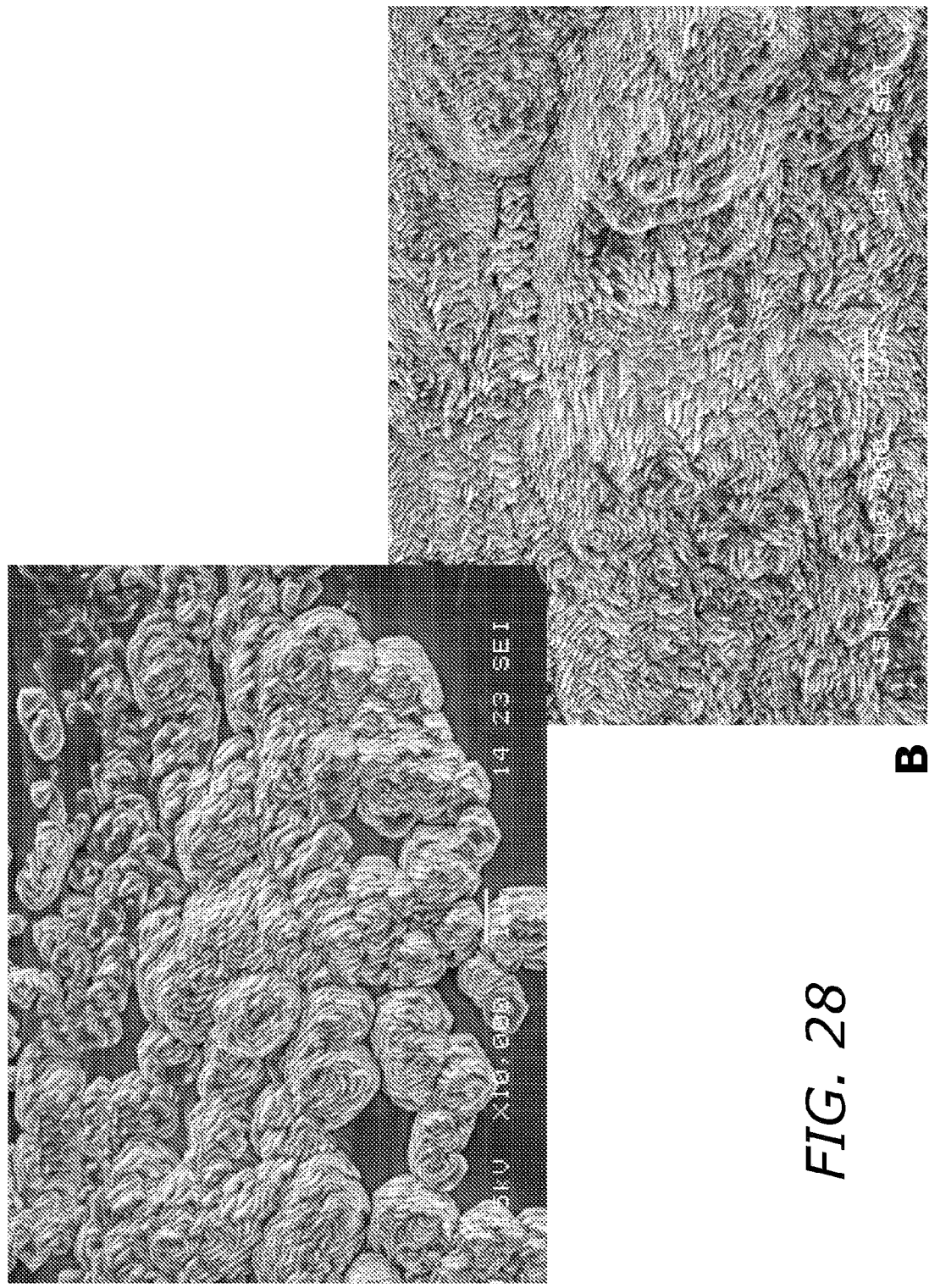
FIG. 28A-C depicts the effects of treatment time on the 'rose' morphology at 5 minutes (FIG. 28A) and 10 minutes (FIG. 28B) according to the teachings of the present invention.
Figure 28:
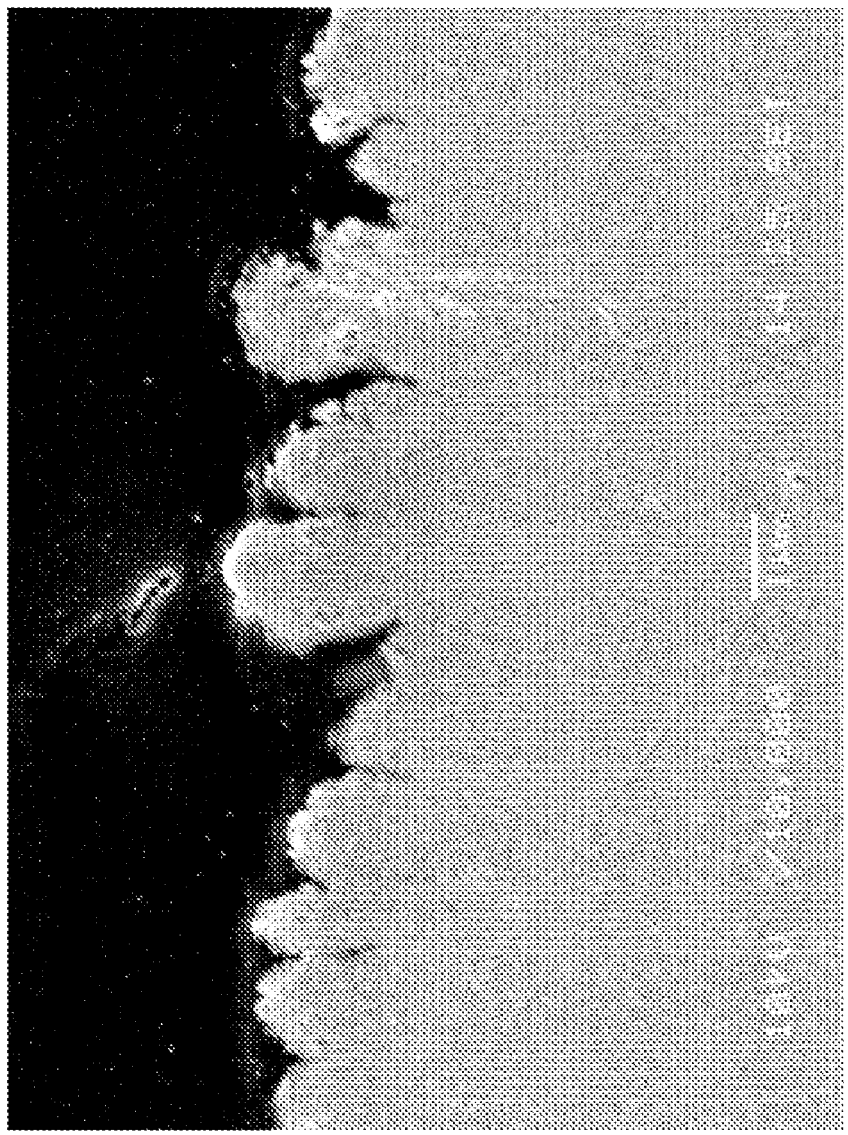

FIG. 26 depicts the pillar morphology in from above (FIG. 26A) and in cross-section (FIG. 26B). FIG. 27 depicts a three-dimensionally interconnected porous structure at low magnification (FIG. 27A), high magnification from above (FIG. 27B) and high magnification in cross-section (FIG. 27C). Furthermore, FIG. 8 depicts texturing of MP35N stents to yield the related morphologies from Group 1, cantaloupe (FIG. 8A), brain (FIG. 8B) and three dimensional interconnecting porous structure (FIG. 8E).

In this Example, temperature was controlled by controlling RF power. However, temperature can be controlled by any means which results in temperature changes of the substrate, such as, but not limited to, RF frequency, heat sinks, thermal mass of the substrate, and substrate placement location relative to the electrodes or any combination thereof. FIG. 25 depicts the substrate as it changes from pillars to three dimensional interconnected porous structure over time. As the substrate temperature is increased, individual pillars (FIG. 25A) start coalescing to form connected pillars (FIG. 25B). At this stage, the number of pillars per unit area decreases from approximately 13/µm² to 1/µm², while the average diameter of pillars increases from approximately 0.2 µm to 1.2 µm. Also, the height of pillars increases from approximately 1 µm to 2 µm. As more pillars connected, the aspect ratio increases from 1 (circular) to almost 23 (elongated). With a further increase of temperature, the pillars become even more connected and the spacing between them becomes larger. At one point, the morphology of the connected pillars and the spacing resembles interdendritic eutectic structures or 'brain' (FIG. 25B). With further increase in temperature, the spacing becomes larger and round pores start forming in the 'cantaloupe' configuration (FIG. 25C). With even further increases in temperature, undercuts start developing and three dimensionally interconnected porous (3D porous) structures are formed (FIG. 25D). In the three-dimensionally interconnected porous structures, pore size ranges from 0.6 µm to 4.2 µm, and some elongated pores have their aspect ratio up to 11. The depth of this structure can range from 2 µm to 4 µm. Pores are randomly interconnected through the depth, thus forming the three dimensional porous structure. Percent porosity of this structure can be estimated from two dimensional cross-section images using any image analysis software, and can range approximately from 30% to 80%.

The microstructural characteristics of the pillar/3D porous structure morphologies are shown in Table 1. Number density refers to the number of microstructural features per unit area, square microns in this experiment. Aspect ratio is the ratio between the length of the major axis and minor axis of the elongated microstructural features.

TABLE 1

Microstructural characteristics of pillar and 3D porous morphologies

| Texture | Number density range (per µm²) | Average number density | Diameter range (µm) | Average diameter | Height (µm) | Aspect ratio |
|---|---|---|---|---|---|---|
| Pillar | 6-28 | 12.9 | 0.07-0.36 | 0.2 | 1-2 | — |
| Connected pillar (brain) | 0.9-1.3 | 1.2 | 0.2-8.4 | 1.2 | 2-3 | 23 |
| 3D porous structure* | 0.4-0.7 | 0.6 | 0.6-4.2 | 1.3 | 2-4 | 11 |

*For the 3D porous structure morphology, the measurements are of the pores rather than other microstructural features.

Example 7

Effect of Treatment Time on Texture Morphology

An exemplary scanning electron micrograph of rose morphology (Group 2) is depicted in FIG. 8D. The characteristics of the rose morphology changes with treatment time (FIG. 28A-C). As treatment time increases, the number of roses per unit area and the average diameter of roses increase. The number of roses per unit area ranges from 0.6/µm² to 1.2/µm², and the diameter of roses ranges from 1.2 µm to 2.1 µm. The height of roses range from 0.3 µm to 2.0 µm (FIG. 28C). Each rose has approximately 10 to 20 nanometer size leaflets with the width ranging from 0.09 µm (90 nm) to 0.15 mm (150 nm). With further treatment, roses start touching and the entire substrate surface becomes covered with the rose structures (FIG. 28B). However, the width of leaflets does not appear to change greatly with treatment time. The textured microstructural characteristics of the rose morphology are shown in Table 2.

TABLE 2

Microstructural characteristics of rose morphology

| Texture | Number density range (per µm²) | Avg. number density | Diameter range (µm) | Avg. diameter | Leaflet thickness range (µm) | Avg. leaflet thickness | Height range | Avg. Height |
|---|---|---|---|---|---|---|---|---|
| Rose | 0.6-1.2 | 0.9 | 1.2-2.1 | 1.7 | 0.09-0.15 | 0.13 | 0.3-2.0 | 1.4 |

Example 8

Generation of Volcano Morphology on Ti-6Al-4V Alloy Substrate

An exemplary scanning electron micrograph of volcano morphology (Group 3) is depicted in FIG. 17A-D. A Ti-6Al-4V pin was textured and the microstructural characteristics determined as above and presented in Table 3.

TABLE 3

Microstructural characteristics of textured Ti—6Al—4V

| Texture | Number density range (per µm²) | Average number density | Pore diameter range (µm) | Average pore diameter | Aspect ratio |
|---|---|---|---|---|---|
| Volcano* | 1.9-2.6 | 2.3 | 0.03-3.54 | 0.29 | 14.2 |

*For the volcano morphology, the measurements are of the pores rather than other microstructural features.

Example 9

Loss of Substrate Material After Texturing

To study whether there was loss of substrate material after surface texturing, MP35N alloy wires and stents were weighed before and after texturing for 1 minute and 10 minutes.

Plasma texturing conditions were 400 Volts power, 30 sccm Ar flow resulting in 39 mtorr of pressure, and 1 or 10 minutes of texturing time. The samples were each weighed 3 times before and after texturing. The mass lost was reported as a % of the original mass of the sample. Four MP35N CoCr alloy wire samples of two different lengths were placed on the platen within the chamber. Data for 24 mm lengths of wire is shown in Table 4 below.

Plasma texturing of MP35N CoCr alloy wire for 1 minute under the conditions listed above resulted in a 0.6284% loss of the original mass. Plasma texturing wire for 10 minutes under the same conditions resulted in a 5.0719% loss of the original mass.

TABLE 4

Loss of substrate material after texturing

| Sample # | Texturing time (min) | Mass pre-texture (mg) | Stdev | Mass after texture (mg) | Stdev | Avg % mass lost |
|---|---|---|---|---|---|---|
| Wire 19-1 | 1 | 24.3132 | 0.0003 | 24.1550 | 0.0013 | 0.6284 |
| Wire 19-2 | 1 | 24.2551 | 0.0006 | 24.0972 | 0.0007 | |
| Wire 20-1 | 10 | 24.2214 | 0.0007 | 22.9619 | 0.0008 | 5.0719 |
| Wire 20-2 | 10 | 24.7011 | 0.0001 | 23.4799 | 0.0008 | |

In another set of experiments the mass loss from 24 vascular MP35N alloy stents during texturing was measured.

The stents were textured in 6 separate runs with 4 stents in each run. The plasma texturing conditions were 500 volts of power, 30 sccm of Ar flow resulting in 39 mTorr of pressure, and 10 minutes of texturing time. The average mass lost from the stents was 6.0087% of the original mass.

Example 10

Implantation of Surface-Textured Pins in Dogs

The effects of surface texturing on pins implanted in the femurs of dogs were studied. Six pins are used for analysis as follows: anodized pins, amorphous textured pins, crystalline textured pins, hydroxyapatite coated pins, arsenic machined pins, and HVD textured pins.

The pins discussed above were surgically implanted in the femurs of dogs as follows. Each of the femurs of the dogs was implanted with the six pins discussed above in holes with 3.01 mm diameters. In eight weeks the dogs were weighed and euthanized. The femurs were dissected and removed with each dog donating one femur. The selected femurs were then placed in 10% neutral buffered formalin. The pins were evaluated in pull-out force testing to determine their average and maximum forces for each pin. Pull-out forces were increased in textured pins as opposed to pins without texturing.

Histopathology of the bones (those directly in contact to the pins) was also evaluated to determine compatibility and structural architecture. The reaction bone response was evaluated.

Example 11

Adhesion of Polymer Coatings to Textured Stents

Eighteen millimeter stents were textured resulting in a weight loss of 750 μg. Bare and textured (pre-wetted stents were coated with polymer comprising Matrix™ (a terpolymer of vinyl acetate, hexylmethacrylate, and N-vinylpyrrolidone) or C108 (hexylmethacrylate/hydroxypropylmethacrylate) along with rapamycin (30%). The coated polymers were evaluated for durability (crimping/tracking/expanding) by scanning electron microscopy (SEM).

Textured stents coated with the Matrix™ polymer and rapamycin exhibited no delamination. Durability is ranked on a scale from 1 to 5 with 1 being the most durable and 5 being the least durable. Matrix™-coated bare stents had a durability ranking of 2/3 and Matrix-coated textured stents had a durability ranking of 2.

Textured stents coated with the C108 polymer and rapamycin exhibited no delamination. C108-coated bare stents (FIG. 30A) had a durability ranking of 5 and C108-coated textured stents (FIG. 30B) had a durability ranking of 2/3.

Therefore, texturing the surface of a stent promotes adhesion and durability of drug-containing polymers on the stent surface.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for providing a medical device with a non-random textured surface comprising;
   placing a medical device in a plasma chamber;
   reducing the atmospheric pressure within said plasma chamber to provide a process pressure of less than approximately 760 Torr;
   providing a non-reactive gas to said plasma chamber while maintaining said process pressure of less than approximately 760 Torr; and
   exposing said medical device to said gas phase plasma to achieve surface heating of said device to the point where the surface glows, thereby producing a non-random textured surface on said medical device.

2. A method for providing a medical device with a non-random textured surface comprising;
   placing a medical device in a plasma chamber;
   reducing the atmospheric pressure within said plasma chamber to provide a process pressure of less than approximately 760 Torr;
   providing a non-reactive gas to said plasma chamber while maintaining said process pressure of less than approximately 760 Torr;
   applying sufficient power to an radio frequency (RF) source to generate sufficient RF energy in said plasma chamber to generate a gas-phase plasma
   providing at least one additional heat source; and
   exposing said medical device to said gas phase plasma and said at least one additional heat source to achieve surface heating of said device to the point where the surface glows, thereby producing a non-random textured surface on said medical device.

3. The method according to claim 2 wherein said process pressure ranges from approximately 2 mTorr to approximately 400 mTorr.

4. The method according to claim 2 wherein said RF frequency comprises frequencies from approximately 10 KHz to approximately 80 MHz.

5. The method according claim 2 wherein in said non-reactive gas is selected from the group consisting of nitrogen, helium, neon, argon, krypton, xenon and radon.

6. The method according to claim 5 wherein said non-reactive gas is argon.

7. The method according to claim 2 wherein said RF frequency is generated from an RF-biased stage and wherein said RF frequency is continuous, pulsed or any combination thereof.

8. The method according to claim 2 wherein said applying step further comprises isolating said medical device from said RF frequency source.

9. The method according to claim 2 wherein said applying step further comprises placing said medical device in direct contact with said RF frequency source.

10. The method according to claim 2 wherein said power comprises wattages of between approximately 5 W and approximately 5000W.

11. The method according to claim 10 wherein said power comprises wattages of between approximately 100 W and approximately 1000 W.

12. The method according to claim 2 wherein said RF frequency is between approximately 40 KHz to approximately 28 MHz.

13. The method according to claim 12 wherein said RF frequency is between approximately 2 MHz and approximately 14 MHz.

14. The method according to claim 2 wherein said process pressure is achieved with non-reactive gas flows of about 2 sccm and about 150 sccm.

15. The method according to claim 2 wherein said medical device is selected from the group consisting of neurostimulators, catheters, cardiac valves, shunts, pacemakers, implantable cardioverter defibrillators, vascular stents, stent grafts, drug-delivery devices, bone screws, bone covers, spinal plates, tracheal stents, medical prosthesis, feeding tubes, trocar needles, clamps, and forceps.

16. The method of claim 15 wherein said medical device comprises materials selected from the group consisting of stainless steel, MP35N alloy, Pt—Ir, commercially pure titanium (CP Ti), tantalum, nickel titanium alloys, Ti-6Al-4V, cobalt chrome alloys, zirconium, zirconium alloys, molybdenum alloys and combinations thereof.

17. The method according to claim 2 wherein said at least one additional heat source is provided by RF-field effect, kinetic energy, electromagnetic radiation, induction energy, resistive heat energy or laser energy.

18. A method for providing a medical device with a non-random textured surface comprising;
   placing a medical device in a plasma chamber;
   reducing the atmospheric pressure within said plasma chamber to provide a process pressure of between approximately 100 Torr and approximately $10^{-9}$ Torr;
   providing a stream of argon gas at between approximately 2 sccm and about 150 sccm to said plasma chamber while maintaining said process pressure of between approximately 100 Torr and approximately $10^{-9}$ Torr;
   applying between approximately 100 W and approximately 1000 W of power to an radio frequency (RF) source to generate an RF frequency of between approximately 2 MHz and approximately 14 MHz;
   providing at least one additional heat source;
   exposing said medical device to said heat source to achieve surface heating; and
   maintaining said surface heating for a time of between approximately 1 minute and 20 minutes to achieve a surface glow, thereby producing a non-random textured surface on said medical device.

19. The method according to claim 18 wherein said process pressure is between $10^{-2}$ and $^{-5}$ Torr.

20. The method according to claim 18 wherein said RF frequency is 13.56 MHz.

21. The method according to claim 18 wherein said at least one additional heat source is provided by RF-field effect, kinetic energy, electromagnetic radiation, induction energy, resistive heat energy or laser energy.

22. A method for providing a non-random texture on a medical device with a combined system of inductively coupled plasma and induction heating comprising:
   placing a medical device in a plasma chamber;
   wrapping an induction coil around said medical device;

applying power though said induction coil resulting in the heating of said medical device;

reducing the atmospheric pressure within said plasma chamber to provide a process pressure of less than approximately 760 Torr;

providing a non-reactive gas to said plasma chamber while maintaining said process pressure of less than approximately 760 Torr; and exposing said medical device to said gas phase plasma to achieve surface heating of said device to the point wherein the surface glows, thereby producing a non-random textured surface on said medical device.

23. The method according to claim 22 wherein said medical device is selected from the group consisting of implantable medical devices, leads, vascular stents, dental wires, dental screws, artificial temporomandibular joints, bone screws, plates, hip prosthesis, bone nails, wires, pins, artificial knee implants, tubular pins, spinal implants, ophthalmic drug delivery devices, ophthalmic rods, surgical tools, dental implants, orthopedic implants and micro-abrasion devices.

24. The method according to claim 22 wherein said medical device is comprised of a material selected from the group consisting of metals, metal alloys, polymers and ceramics.

25. The method according to claim 22 wherein said power is applied to said induction coil in alternating current, resulting in a magnetic field.

26. The method according to claim 25 wherein said power is applied to said induction coil at an alternating current frequency of between approximately 1 kHz and approximately 60 MHz.

27. The method according to claim 26 wherein said frequency is between approximately 5 kHz and approximately 30 kHz and said surface texturing penetrates said medical device deeply.

28. The method according to claim 26 wherein said frequency is between approximately 100 kHz and approximately 500 kHz and said surface texturing penetrates said medical device shallowly.

29. The method according to claim 26 wherein said frequency is between approximately 400 kHz and approximately 60 MHz.

30. The method according to claim 22 wherein said induction heating and said plasma generation systems each have their own RF power supply.

31. The method according to claim 30 wherein each RF power supply generates a different RF frequency.

* * * * *